(12) United States Patent
Taggart

(10) Patent No.: US 9,849,204 B2
(45) Date of Patent: Dec. 26, 2017

(54) STERILIZATION DEVICE AND METHODS

(71) Applicant: STERIO3, LLC, Madison, WI (US)

(72) Inventor: Daniel Taggart, Salt Lake City, UT (US)

(73) Assignee: STERIO3, LLC, Madison, WI (US)

( * ) Notice: Subject to any disclaimer, the term of this patent is extended or adjusted under 35 U.S.C. 154(b) by 0 days.

(21) Appl. No.: 15/406,363

(22) Filed: Jan. 13, 2017

(65) Prior Publication Data

US 2017/0197003 A1    Jul. 13, 2017

Related U.S. Application Data

(60) Provisional application No. 62/278,180, filed on Jan. 13, 2016.

(51) Int. Cl.
| | |
|---|---|
| *A61L 2/00* | (2006.01) |
| *G05B 1/00* | (2006.01) |
| *G01D 11/26* | (2006.01) |
| *A61L 9/00* | (2006.01) |
| *A61L 2/20* | (2006.01) |
| *A61L 2/18* | (2006.01) |
| *A61L 2/22* | (2006.01) |

(52) U.S. Cl.
CPC ............... *A61L 2/202* (2013.01); *A61L 2/186* (2013.01); *A61L 2/22* (2013.01); *A61L 2202/13* (2013.01); *A61L 2202/16* (2013.01); *A61L 2202/24* (2013.01)

(58) Field of Classification Search
CPC ........ A61L 2/00; A61L 2/0088; A61L 2/0094; A61L 2/186; A61L 2/202; A61L 2/208

USPC ........................ 422/1, 28, 105, 119, 292, 305
See application file for complete search history.

(56) References Cited

U.S. PATENT DOCUMENTS

| | | |
|---|---|---|
| 3,704,096 A | 11/1972 | Karlson et al. |
| 4,372,916 A | 2/1983 | Chamberlain et al. |
| 4,550,010 A | 10/1985 | Chelu |
| 4,642,165 A | 2/1987 | Bier |
| 4,643,876 A | 2/1987 | Jacobs et al. |

(Continued)

FOREIGN PATENT DOCUMENTS

| | | |
|---|---|---|
| CN | 2905066 | 5/2007 |
| KR | 20120093790 A | 8/2012 |

(Continued)

OTHER PUBLICATIONS

Fischbacher, Alexandra et al., "The OH Radical Yield in the H2O2 + O3 (Peroxone) Reaction," Environmental Science & Technology, vol. 47, pp. 9959-9964, 2013.

(Continued)

*Primary Examiner* — Monzer R Chorbaji
(74) *Attorney, Agent, or Firm* — Foley & Lardner LLP

(57) ABSTRACT

Embodiments of the present disclosure generally relate to devices and methods for sterilizing equipment. More particularly, one or more embodiments described in the present disclosure are directed to portable devices for sterilizing medical equipment in emergency situations. The sterilization devices and method of the present disclosure address an unmet need for sterilizing surgical equipment in a manner that is not only effective and time-efficient, but is also portable and reliable enough to use in emergency medical situations in remote locations where modern sterilization equipment is not available.

28 Claims, 12 Drawing Sheets

(56) References Cited

U.S. PATENT DOCUMENTS

| | | | |
|---|---|---|---|
| 5,207,237 A | 5/1993 | Langford | |
| 5,266,275 A | 11/1993 | Faddis | |
| 5,520,893 A | 5/1996 | Kasting et al. | |
| 5,525,310 A | 6/1996 | Decker et al. | |
| 5,527,508 A | 6/1996 | Childers et al. | |
| 5,667,753 A | 9/1997 | Jacobs | |
| 5,700,426 A | 12/1997 | Schmitthaeusler et al. | |
| 5,855,856 A | 1/1999 | Karlson | |
| 5,904,901 A * | 5/1999 | Shimono | A61L 9/015 422/120 |
| 5,942,438 A | 8/1999 | Antonoplos et al. | |
| 6,096,266 A | 8/2000 | Duroselle | |
| 6,156,267 A | 12/2000 | Pai et al. | |
| 6,365,103 B1 | 4/2002 | Fournier | |
| 6,410,338 B1 | 6/2002 | Lippold et al. | |
| 6,589,479 B2 | 7/2003 | Dufresne et al. | |
| 6,630,105 B1 | 10/2003 | O'Neill et al. | |
| 6,699,434 B1 | 3/2004 | Lukasik et al. | |
| 6,767,509 B1 | 7/2004 | Griesbach | |
| 7,048,887 B2 | 5/2006 | Frost et al. | |
| 7,128,872 B2 | 10/2006 | Robitaille et al. | |
| 7,186,371 B1 | 3/2007 | Watling | |
| 7,582,257 B2 | 9/2009 | Bedard et al. | |
| 7,588,720 B2 | 9/2009 | Turcot et al. | |
| 7,608,217 B2 | 10/2009 | Champagne | |
| 7,892,486 B2 * | 2/2011 | Mizuno | A61L 2/14 422/33 |
| 8,529,832 B2 | 9/2013 | Lee | |
| 8,540,943 B2 | 9/2013 | Kee et al. | |
| 8,683,401 B2 | 3/2014 | Onodera | |
| 8,841,440 B2 | 9/2014 | Chu et al. | |
| 8,945,467 B2 | 2/2015 | Soberon et al. | |
| 2002/0012610 A1 | 1/2002 | Dufresne et al. | |
| 2003/0196678 A9 | 10/2003 | Torek et al. | |
| 2004/0077917 A1 | 4/2004 | Centanni et al. | |
| 2005/0147527 A1 | 7/2005 | Brown et al. | |
| 2006/0099121 A1 | 5/2006 | Doona et al. | |
| 2007/0065335 A1 | 3/2007 | Bedard et al. | |
| 2007/0221582 A1 | 9/2007 | Holland et al. | |
| 2007/0231199 A1 | 10/2007 | Lin et al. | |
| 2008/0014113 A1 | 1/2008 | Centanni | |
| 2008/0233002 A1 | 9/2008 | Mizuno et al. | |
| 2011/0076191 A1 | 3/2011 | Gordon et al. | |
| 2011/0076192 A1 | 3/2011 | Robitaille et al. | |
| 2011/0085934 A1 | 4/2011 | Joshi et al. | |
| 2013/0236355 A1 | 9/2013 | Dufresne et al. | |
| 2013/0243649 A1 | 9/2013 | Dufresne et al. | |
| 2015/0352238 A1 | 12/2015 | Dufresne et al. | |

FOREIGN PATENT DOCUMENTS

| | | |
|---|---|---|
| WO | 2005035067 A2 | 4/2005 |
| WO | 2015135887 A1 | 9/2015 |
| WO | 2016025934 A1 | 2/2016 |

OTHER PUBLICATIONS

James, Patrick "Improved Electrolytic Hydrogen Peroxide Generator," www.defensetechbriefs.com, Jul. 1, 2005, 1 page.

Sterizone® VP4 Sterilizer, TSO3 Inc., Québec, Canada, acquired Apr. 24, 2015, 28 pages.

International Search Report and Written Opinion issued in PCT Application No. PCT/US2017/013525, dated Apr. 28, 2017, 12 pages.

* cited by examiner

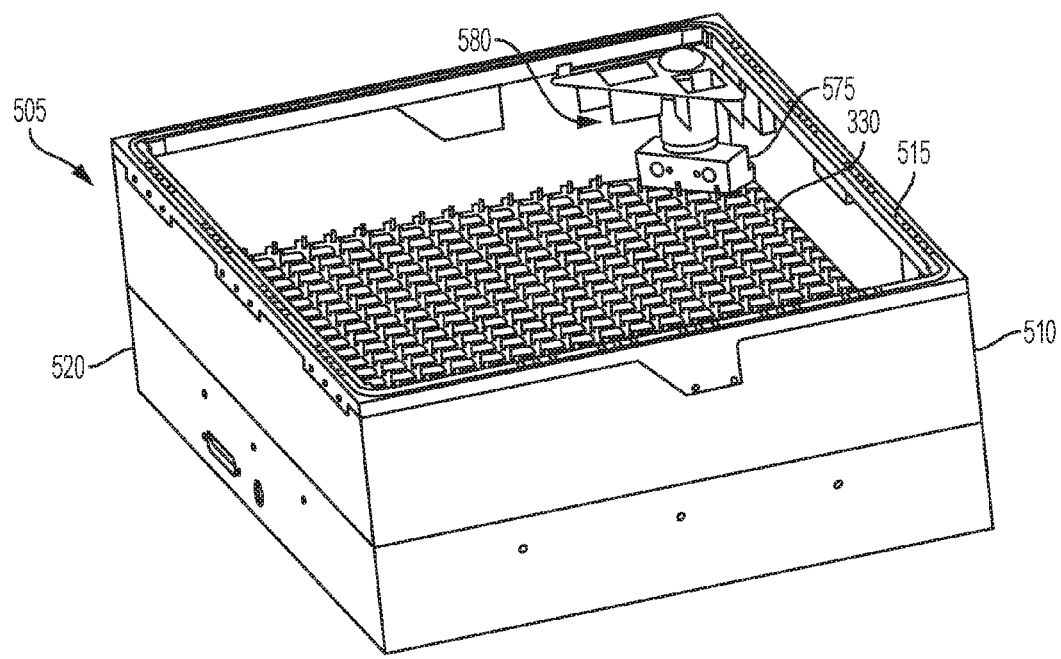
FIG. 8
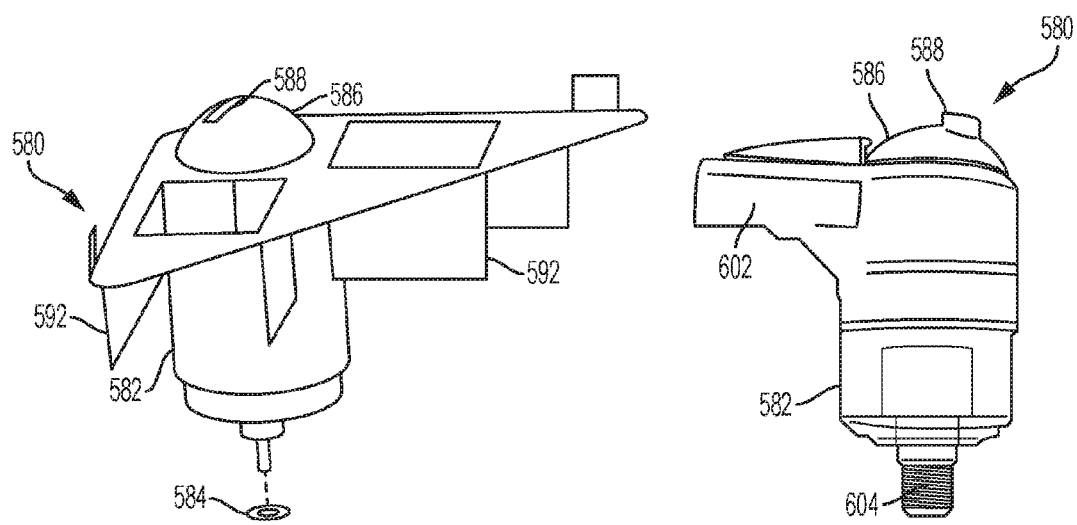
FIG. 9A
FIG. 9B

STERILIZATION DEVICE AND METHODS

PRIORITY

This non-provisional patent application claims priority to and the benefit of U.S. Provisional Patent Application Ser. No. 62/278,180, filed Jan. 13, 2016, entitled "STERILIZATION DEVICE AND METHOD." The foregoing provisional patent application is incorporated herein by reference in its entirety for all purposes.

FEDERALLY FUNDED RESEARCH

Some embodiments of the invention disclosed herein were made with government support under Grant No. FA8650-13-C-6376 awarded by the Department of Defense. The U.S. Government has certain rights in the invention.

FIELD

Embodiments of the present disclosure generally relate to devices and methods for sterilizing medical equipment. In particular, the present disclosure provides portable devices for sterilizing surgical equipment, such as in emergency medical situations, as well as in remote locations where modern sterilization equipment is not available.

BACKGROUND

Contaminated surgical equipment can result in secondary complications ranging from surgical site infections to death. Consequently, surgeons require effective and dependable sterilization devices to ensure that their surgical equipment and instruments are sterile. In many cases, it is also important that sterilization devices effectively sterilize surgical equipment in a timely manner, especially in emergency medical situations such as natural disasters and battlefields. Current sterilization devices typically use steam sterilization, which has several drawbacks that make these devices and methods unsuitable for use in emergency medical situations, including the requirement for potable water, access to a power source, and a lack of portability. Therefore, there is a need for improved devices and methods for sterilizing surgical equipment in a manner that is not only effective and time-efficient, but also provides sufficient portability and reliability to use in emergency medical situations in remote locations where modern sterilization equipment may not available.

SUMMARY

Embodiments of the present disclosure include a portable sterilization device. In some embodiments, the portable sterilization device comprises: an external housing unit; a sealable sterilization chamber located within the external housing unit; a sterilant delivery device operatively associated with the sterilization chamber, the sterilant delivery device comprising a nebulization element and one or more sterilants, wherein the nebulization element is configured to convert the one or more sterilants into an oxidative aerosol sterilant and deliver the oxidative aerosol sterilant into the sterilization chamber; an ozone delivery device operatively associated with the sterilization chamber and the sterilant delivery device, the ozone delivery device configured to deliver ozone into the sterilization chamber; an airflow circulation assembly; a control panel configured to operate the sterilization chamber, the sterilant delivery device, the ozone delivery device, and the airflow circulation assembly; and a power source operatively associated with the control panel and configured to supply power to the sterilization chamber, the sterilant delivery device, the ozone delivery device, and the airflow circulation assembly; whereupon activation, the control panel is configured to execute an operation to provide simultaneous delivery of the oxidative aerosol sterilant and the ozone into the sterilization chamber.

The portable sterilization device as described herein above, wherein the sterilization chamber is configured to accept a plurality of medical instruments, and wherein the simultaneous delivery of the oxidative aerosol sterilant and the ozone into the sterilization chamber containing the plurality of medical instruments at a pre-determined ozone concentration for a pre-determined time period is sufficient to obtain a sterility assurance level (SAL) of $10^{-6}$ for inactivation of a 6 log population of organisms determined to be most resistant organisms (MRO) to sterilization.

The portable sterilization device as described herein above, wherein the one or more sterilants comprise hydrogen peroxide.

The portable sterilization device as described herein above, wherein at least a portion of the sterilant delivery device comprising the nebulization element is contained within the sterilization chamber.

The portable sterilization device as described herein above, wherein the one or more sterilants comprise hydrogen peroxide contained within the nebulization element.

The portable sterilization device as described herein above, wherein the ozone delivery device comprises a corona discharge ozone generator.

The portable sterilization device as described herein above wherein the airflow circulation assembly comprises one or more pumps configured to circulate air through the sterilization device.

The portable sterilization device as described herein above, further comprising a sterilant remediation element, wherein the sterilant remediation element and the airflow circulation assembly are operatively associated with the sealable sterilization chamber; and wherein the airflow circulation assembly is configured to cause air to flow from the sterilization chamber through the sterilant remediation element such that the air comprising the combination of the one or more sterilants and the ozone passes through the sterilant remediation element to facilitate breakdown of the one or more sterilants and the ozone into oxygen and water.

The portable sterilization device as described herein above, wherein the sterilant remediation element comprises a metal-based catalyst that facilitates breakdown of the one or more sterilants and the ozone into oxygen and water.

The portable sterilization device as described herein above, further comprising one or more sensors operatively associated with the control panel and configured to monitor one or more operational parameters of the device.

The portable sterilization device as described herein above, wherein the one or more operational parameters comprise one or more of closure integrity, sterilant levels, ozone levels, airflow velocity, air pressure, valve operation, temperature, humidity, power levels, electrical current, device operation, sterilization cycle lengths, and sterilization cycle number.

Embodiments of the present disclosure include a sterilization chamber for sterilizing a plurality of medical instruments. In some embodiments the sterilization chamber comprises: an instrument receptacle comprising a sealing mechanism; at least one ozone inlet; at least one airflow outlet; and a sterilant delivery device comprising a nebulization element and one or more sterilants, wherein the nebulization element is configured to convert the one or more sterilants into an oxidative aerosol sterilant and deliver the oxidative aerosol sterilant into the instrument receptacle.

The sterilization chamber as described herein above, wherein the one or more sterilants comprise hydrogen peroxide.

The sterilization chamber as described herein above, further comprising an ozone delivery device operatively associated with the nebulization element, wherein the ozone delivery device and the nebulization element are configured to deliver the oxidative aerosol sterilant and ozone simultaneously into the instrument receptacle.

The sterilization chamber as described herein above, further comprising an airflow circulation assembly comprising one or more pumps configured to circulate air through the sterilization chamber.

Embodiments of the present disclosure include a method comprising manufacturing a portable sterilization device. In some embodiments the method comprising manufacturing a portable sterilization device comprises: an external housing unit; a sealable sterilization chamber located within the external housing unit; a sterilant delivery device operatively associated with the sterilization chamber, the sterilant delivery device comprising a nebulization element and one or more sterilants, wherein the nebulization element is configured to convert the one or more sterilants into an oxidative aerosol sterilant and deliver the oxidative aerosol sterilant into the sterilization chamber; an ozone delivery device operatively associated with the sterilization chamber and the sterilant delivery device, the ozone delivery device configured to deliver ozone into the sterilization chamber; an airflow circulation assembly; a control panel configured to operate the sterilization chamber, the sterilant delivery device, the ozone delivery device, and the airflow circulation assembly, wherein the control panel is further configured to execute an operation to deliver the oxidative aerosol sterilant and the ozone simultaneously into the sterilization chamber; and a power source operatively associated with the control panel and configured to supply power to the sterilization chamber, the sterilant delivery device, the ozone delivery device, and the airflow circulation assembly.

The method as described herein above, wherein at least a portion of the one or more sterilants comprise hydrogen peroxide.

The method as described herein above, wherein the sterilant delivery device comprising the nebulization element is at least partially contained within the sterilization chamber.

The method as described herein above, wherein the one or more sterilants comprise hydrogen peroxide contained within the nebulization element.

The method as described herein above, wherein the ozone delivery device comprises a corona discharge ozone generator.

The method as described herein above, wherein the airflow circulation assembly comprises one or more pumps configured to circulate air through the sterilization device.

The method as described herein above, wherein the portable sterilization device further comprises a sterilant remediation element, wherein the sterilant remediation element and the airflow circulation assembly are operatively associated with the sealable sterilization chamber; and wherein the airflow circulation assembly is configured to cause air to flow from the sterilization chamber through the sterilant remediation element such that the air comprising the combination of the one or more sterilants and the ozone passes through the sterilant remediation element to facilitate breakdown of the one or more sterilants and the ozone into oxygen and water.

The method as described herein above, wherein the sterilant remediation element comprises a metal-based catalyst that facilitates breakdown of the one or more sterilants and the ozone into oxygen and water.

The method as described herein above, wherein the portable sterilization device further comprises one or more sensors operatively associated with the control panel and configured to monitor one or more operational parameters of the device.

The method as described herein above, wherein the one or more operational parameters comprise one or more of closure integrity, sterilant levels, ozone levels, airflow velocity, air pressure, valve operation, temperature, humidity, power levels, electrical current, device operation, sterilization cycle lengths, and sterilization cycle number.

The terms "determine," "calculate," and "compute," and variations thereof, as used herein, are used interchangeably and include any type of methodology, process, mathematical operation or technique.

It is to be noted that the term "a" or "an" entity refers to one or more of that entity. As such, the terms "a" (or "an"), "one or more" and "at least one" can be used interchangeably herein. It is also to be noted that the terms "comprising," "including," and "having" can be used interchangeably.

Unless otherwise specified, any use of any form of the terms "connect," "engage," "couple," "attach," or any other term describing an interaction between elements is not meant to limit the interaction to direct interaction between the elements and may also include indirect interaction between the elements described. In the following discussion and in the claims, the terms "including" and "comprising" are used in an open-ended fashion, and thus should be interpreted to mean "including, but not limited to . . . ." The various characteristics mentioned above, as well as other features and characteristics described in more detail herein will be readily apparent to those skilled in the art with the aid of the present disclosure upon reading the following detailed description of the embodiments.

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C," and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "means" as used herein shall be given its broadest possible interpretation in accordance with 35 U.S.C. §112(f). Accordingly, a claim incorporating the term "means" shall cover all structures, materials, or acts set forth herein, and all of the equivalents thereof. Further, the structures, materials or acts and the equivalents thereof shall include all those described in the summary, brief description of the drawings, detailed description, abstract, and claims themselves.

It should be understood that every maximum numerical limitation given throughout this disclosure is deemed to include each and every lower numerical limitation as an alternative; as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

FIG. 8 is a representative illustration of a sterilization chamber for a sterilization device according to an example aspect;

FIG. 9A is a representative illustration of a sterilant delivery device for a sterilization device according to an example aspect;

FIG. 9B is a representative illustration side view of a sterilant delivery device for a sterilization device according to an example aspect;

DETAILED DESCRIPTION

Embodiments of the present disclosure generally relate to devices and methods for sterilizing medical equipment. In particular, the present disclosure provides portable devices for sterilizing surgical equipment in emergency medical situations, including in remote locations where modern sterilization equipment is not available. For example, emergency medical personnel such as combat medics can benefit from the various advantages of the devices and methods of the present invention, which include features such as process automation and feedback, safety features, an intuitive control interface, process reliability, minimal power requirements, and battery-powered operation. Embodiments of the present disclosure can be referred to as a rugged ozone sterilization system (ROSS) and are configured to meet a critical need for sterilization in portable hospitals, initial treatment and assessment areas, field units and establishments that lack sterilization or disinfection infrastructure. In some embodiments, devices of the present disclosure sterilize surgical instruments quickly at ambient temperature, under battery power, or available AC, using a pre-measured packet of hydrogen peroxide and on-board generated ozone from local air.

In an example aspect, devices of the present disclosure solve the problem of sterilization of surgical instruments or medical equipment in remote locations or areas, for example areas following natural disasters such as an earthquake, hurricane, flood or tsunami, or in war-torn regions for use by medics or field hospitals. In an example aspect, devices of the present disclosure are useful as low-temperature terminal sterilization of medical devices, dental and veterinary device sterilization, and disinfection generally. Advantageously, the device includes process automation and feedback, safety features, an intuitive control interface, process reliability, minimal power requirements, and battery-powered operation to benefit the user. In an example aspect, devices of the present disclosure increase the availability of sterile surgical instruments due to its highly portable, rugged design and quick process times thus allowing healthcare personnel to continue to treat the critically injured and improve the survival rate of the wounded in Forward Operating Bases and areas of need worldwide.

Figure 1A:
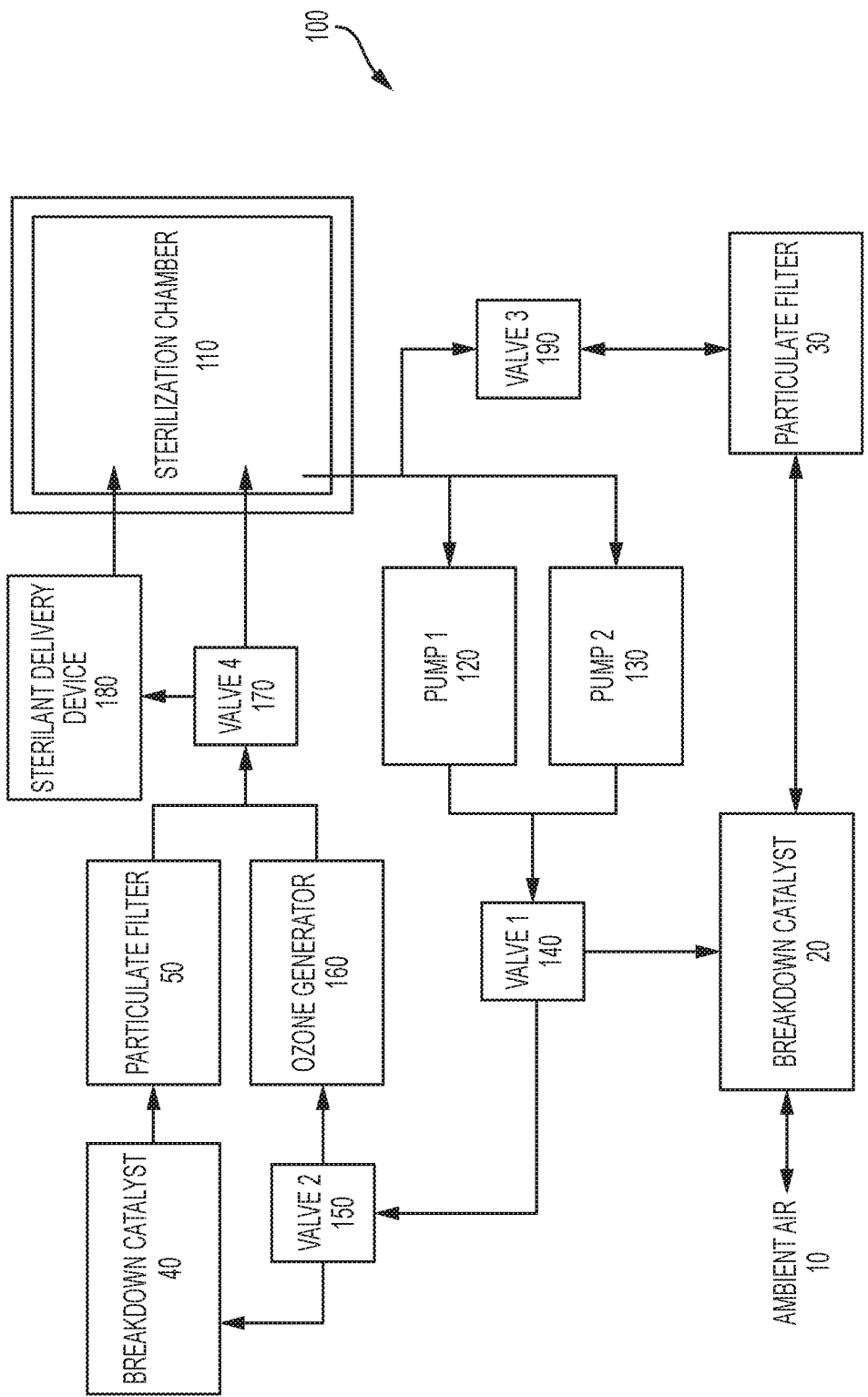
FIG. 1A is a representative illustration of a block flow diagram according to one aspect of the invention.

As illustrated in the flow diagram of FIG. 1A, embodiments of the present disclosure include sterilization device 100. In an example aspect, sterilization device 100 is evacuated in order to reach operational vacuum. In other words, sterilization device 100 operates at a vacuum relative to ambient pressure. The relative vacuum is maintained beyond a specified threshold during the cycle; the threshold is useful as a method of leak detection. A feedback display (as shown on sterilization top of FIG. 3) will indicate if vacuum is insufficient for sterilization to be successful. In an example aspect, sterilization chamber 110 includes a base sealingly engaged to a top via a seal or an o-ring (as shown as element 515 in FIG. 8). The time required for evacuation is relatively short, i.e. about 30 seconds.

Remaining air within sterilization device 100 is useful in the operation of the device. Air from sterilization chamber 110 is directed through pumps 120 and/or 130 and through valve 140, upon which valve 140 is closed to prevent leaks to ambient air 10. The air flow is then directed to ozone generator 160 via valve 150 to provide air containing ozone, which is diverted via valve 170 through sterilant delivery device 180 to simultaneously mix and aerosolize with a dilute liquid sterilant. In an example aspect, the air containing ozone, also referred to as plasma gas sterilant interchangeably herein, is fed to sterilant delivery device 180, which may be a nebulizer, through a nebulizer feed line that is connected to valve 170. Ozone generator 160 is also referred to interchangeably herein as ozone delivery device. In an example aspect, sterilant delivery device 180 is a nebulizer. In an example aspect, sterilant delivery device 180 is a compressive nebulizer. The nebulizer is preloaded or filled with a liquid sterilant. In an example aspect, the liquid sterilant is contained in a nebulizer reservoir. In an example aspect, the liquid sterilant is hydrogen peroxide ($H_2O_2$). In an example aspect, the liquid sterilant is a 7% hydrogen peroxide solution. Sterilant concentrations are increased to an effective threshold level during the simultaneous sterilant injection of air containing ozone mixed with a liquid sterilant such as hydrogen peroxide solution. In an example aspect, sterilant delivery device 180 delivers or injects an aerosolized oxidative sterilant directly to sterilization chamber 110. In an example aspect, the aerosolized oxidative sterilant includes a simultaneously mixed combination of air containing ozone mixed with sterilant such as hydrogen peroxide solution. The time required for sterilant injection is about 7 minutes. Assurances are in place to indicate the unlikely event of a nebulizer failure. The backpressure in the nebulizer feed line is available under "Process Info" of the feedback display. If pressure falls below threshold backpressure level of 2 PSI, then the system aborts, initiates breakdown, and gives indication of nebulizer failure. A tight fit between the nebulizer and the manifold is important in preventing failure from occurring.

After a successful sterilant injection phase to achieve sterilant concentration above effective threshold level taking about 3 minutes, sterilant delivery device 180 continuously delivers an effective concentration of the aerosolized mixture of air containing ozone and liquid to sterilant sterilization chamber 110, for about 21.6 minutes, to expose the contents (i.e. surgical instruments) to the effective concentration thus performing sterilization of the contents.

After successful completion of sterilant exposure to the contents, a breakdown process is initiated in order to prepare the system for being unsealed and for the contents to be safely removed, wherein the acceptable ozone concentration upon completion is 0.1 ppmv. During the breakdown operation, air from within the device is diverted through valve 150 to breakdown catalyst 40. Upon completion of the breakdown operation, which requires about 12 minutes, the feedback display will indicate sterilization is complete and indicate that the device may be opened for removal of the contents. A 30 minute timer automatically initiates and the load remains sterile until the user, prompted by the feedback display, presses 'yes' to open. Although thirty minute sterility duration is validated in an example aspect, extended sterility durations are contemplated. This gives the user flexibility to have the sterile instruments available at the needed time. In an example aspect, the system is not vented until initiated by the user. To vent, air is drawn through breakdown catalyst 20 and particulate filter 30, which may be a 5 micrometer filter, through valve 190. The time required for venting is relatively short, i.e. about 30 seconds.

In an example aspect, surgical instruments can be placed in the device, and after a predetermined process time the device can be opened and the surgical tools are ready for immediate use. Advantageously, the tools are already at ambient temperature. In an example aspect, the sterilization device is configured to have a process time of less than one hour. In other embodiments, the process time may be less than forty-five minutes. In yet another embodiment, the process time is between about 20 minutes and about 40 minutes. In an example aspect, the total time for the sterilization device to sterilize the contents is about 36 minutes.

As those skilled in the art will appreciate, the time values set forth in the foregoing paragraphs may vary depending upon a variety of parameters, including equipment performance and capacity.

As illustrated in the flow diagram of FIG. 1B, embodiments of the present disclosure include a sterilization device 200 similar to device 100, except that sterilant delivery device 280 is located within sterilization chamber 210. In an example aspect, sterilant delivery device 280 is a nebulizer. In an example aspect, sterilant delivery device 280 is a compressive nebulizer. The nebulizer is preloaded or filled with a liquid sterilant. The liquid sterilant is contained in a nebulizer reservoir. In an example aspect, the sterilant is hydrogen peroxide ($H_2O_2$). In an example aspect, the sterilant is a 7% hydrogen peroxide solution.

In an example aspect, the sterilization device is portable. Sterilization device is interchangeably herein referred to as portable sterilization device. In an example aspect, the portable sterilization device comprises an external housing unit, a sealable sterilization chamber (110, 210) located within the external housing unit, and a sterilant delivery device (180, 280) operatively associated with the sterilization chamber. In an example aspect, the sterilant delivery device further comprises a nebulization element and one or more sterilants, wherein the nebulization element is configured to convert the one or more sterilants into an oxidative aerosol sterilant and deliver the oxidative aerosol sterilant into the sterilization chamber. In an example aspect, the portable sterilization device further comprises an ozone delivery device or ozone generator (160) operatively associated with the sterilization chamber and the sterilant delivery device. In an example aspect, the ozone delivery device is configured to deliver ozone into the sterilization chamber. In an example aspect, the portable sterilization device further comprises an airflow circulation assembly. In an example aspect, the airflow circulation assembly includes one or more pumps (120, 130), one or more valves (140, 150, 170, 190), inlets, outlets, and tubing connecting the one or more pumps and valves. In an example aspect, the portable sterilization device further comprises a control panel configured to operate the sterilization chamber, the sterilant delivery device, the ozone delivery device, and the airflow circulation assembly. In an example aspect, the portable sterilization device further comprises a power source operatively associated with the control panel and configured to supply power to the sterilization chamber, the sterilant delivery device, the ozone delivery device, and the airflow circulation assembly; whereupon activation, the control panel is configured to execute an operation to provide simultaneous delivery of the oxidative aerosol sterilant and the ozone into the sterilization chamber.

Figure 2A:
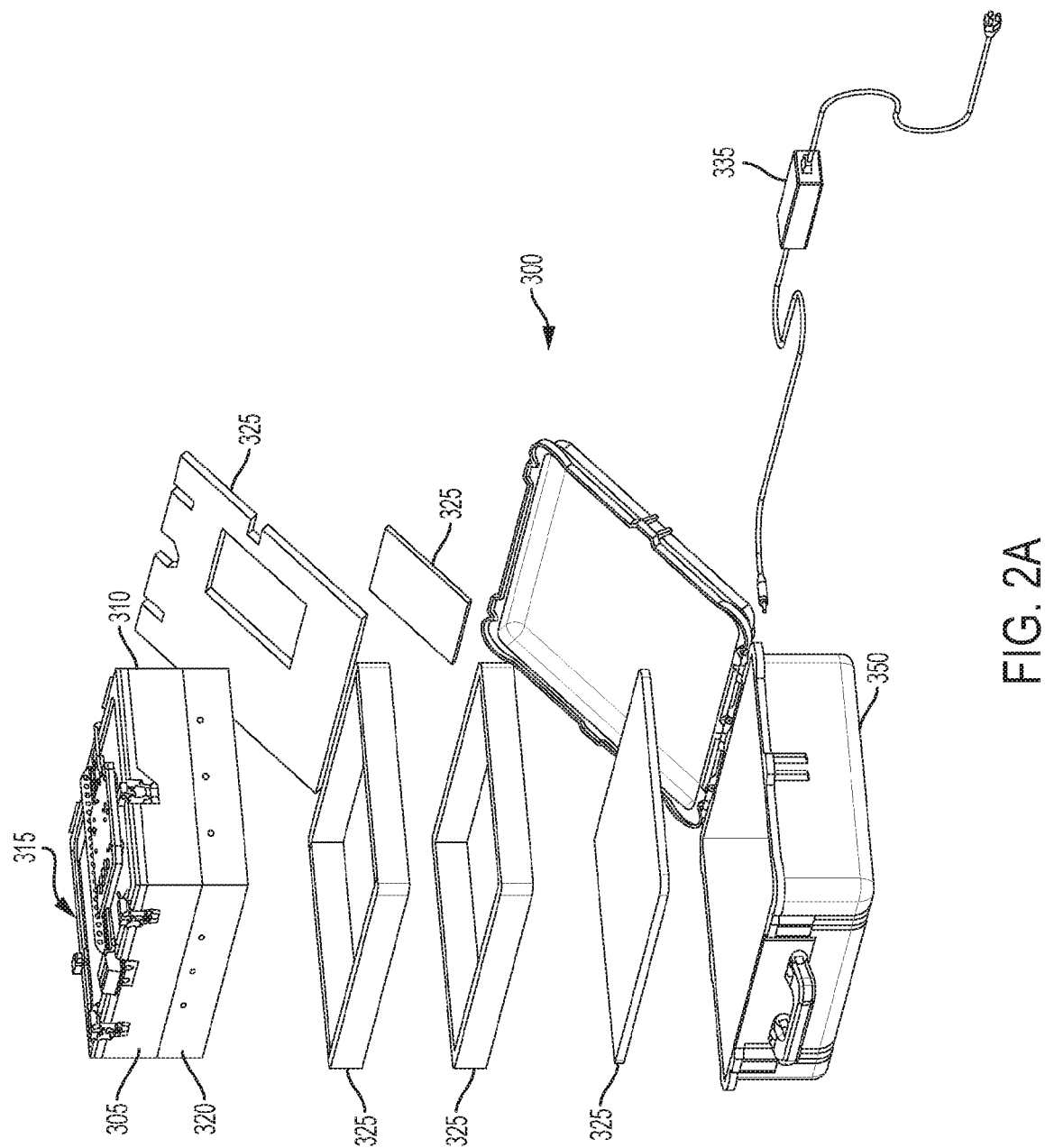
FIG. 2A is a representative illustration exploded view of a sterilization device according to an example aspect.
Figure 2B:
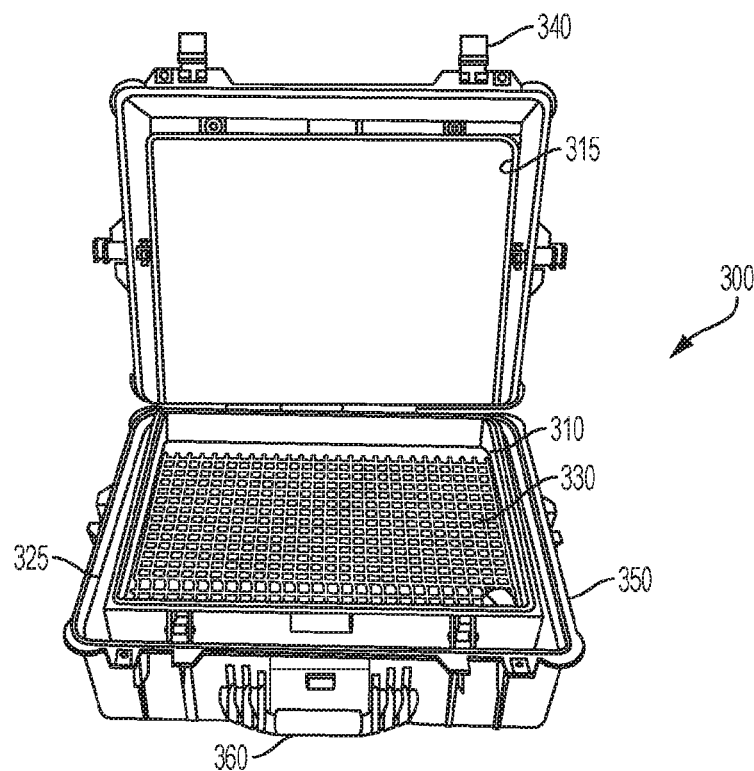
FIG. 2B is a representative illustration of a sterilization device according to an example aspect.

FIG. 2A is a representative illustration exploded view of a sterilization device according to an example aspect. Sterilization device 300 includes housing 350, foam supports 325, assembly of chambers 305, and power adapter 335. Assembly of chambers 305 includes sterilization chamber 310 having top 315 and components chamber assembly 320. As illustrated in FIG. 2B, and according to an example aspect, sterilization device 300 includes case 350. Case 350 is referred to interchangeably herein as external housing or housing. Case 350 is made of any sturdy light weight material or plastic as known in the art, for example, an injection molded impact resistant co-polymer. In an example aspect, case 350 includes an anodized aluminum frame. In an example aspect, case 350 is an external dust proof and water resistant case with no components penetrating or external to the shell. In an example aspect, case 350 is IP67 certified.

Case 350 includes an interior lined with closed cell polyethylene foam support 325, such as foam support sold under the trademark ETHICON®, a trademark owned by the Johnson and Johnson Corporation. Foam support 325 surrounds sterilization chamber 310. There is adequate spacing between the interior of case 350 and sterilization chamber 310 to include foam support and an optional gap. Case 350 includes a top and a bottom and a closing mechanism. Case 350 includes latches hinges, a locking mechanism, or both. Latches hinges 340 are made of a corrosion-resistant material, for example, stainless steel. The locking mechanism may be an electromagnetic locking mechanism or other such mechanism as known in the art. Case 350 also includes handle 360 for ease in portability. Advantageously, device 300 is portable and everything needed for producing sterilant is self-contained. A clean water source is not required and only minimal power requirements are needed in the operation of the sterilization device, thus further enhancing the portability of the device.

In an example aspect, the portable sterilization device includes a sterilization chamber configured to accept a plurality of medical instruments. In an example aspect, the portable sterilization device includes a sterilization chamber configured to accept a plurality of medical instruments wherein the simultaneous delivery of the oxidative aerosol sterilant and the ozone into the sterilization chamber containing the plurality of medical instruments at a pre-determined ozone concentration for a pre-determined time period is sufficient to obtain a sterility assurance level (SAL) of $10^{-6}$ for inactivation of a 6 log population of organisms determined to be most resistant organisms (MRO) to sterilization. In an example aspect, the one or more sterilants comprise hydrogen peroxide.

Figure 2C:
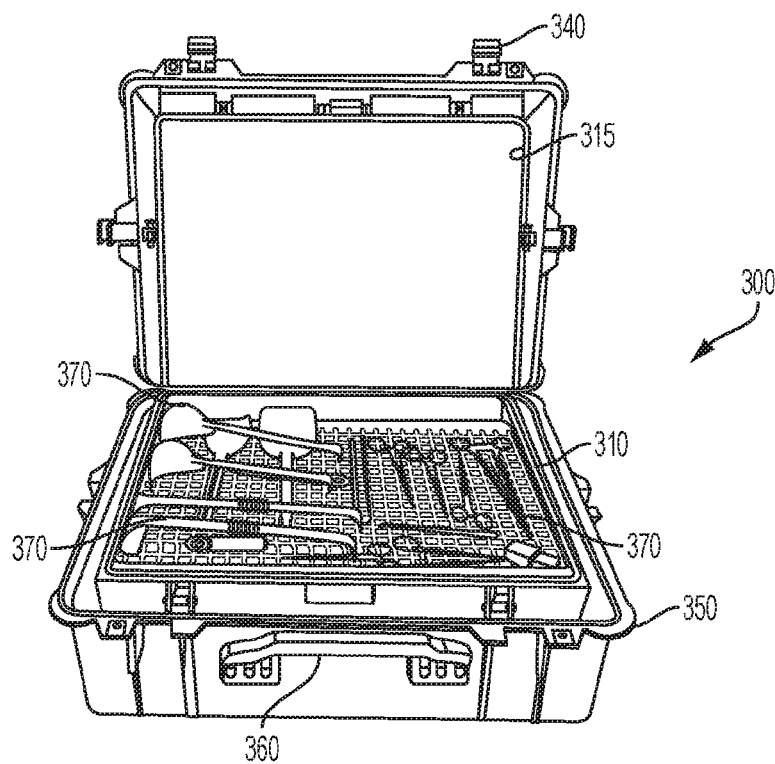
FIG. 2C is a representative illustration of a sterilization device containing surgical instruments according to an example aspect.

As illustrated in FIG. 2C, and according to an example aspect, sterilization device 300 includes sterilization chamber 310. In an example aspect, sterilization chamber 310 is hermetically welded within case 350. In an example aspect, sterilization chamber 310 includes latches hinges, a locking mechanism, or both. Sterilization chamber 310 includes mat 330 to line the interior bottom. Sterilization chamber 310 is configured for receiving surgical instruments 370, or other items, to be sterilized. In an example aspect, surgical instruments 370 are placed upon mat 330, which is silicone or other suitable material. In one embodiment, sterilization is accomplished by an oxidation process facilitated by a sterilant. Advantageously, instruments 370 are exposed to a sterilization process that is non-toxic and does not require high temperatures to inactivate contaminant microorganisms. The sterilization chamber will be described in further detail below including the sterilant delivery device as shown in FIGS. 8 and 9.

In an example aspect, a sterilization chamber for sterilizing a plurality of medical instruments is provided. In an example aspect, the sterilization chamber comprises an instrument receptacle comprising a sealing mechanism; at least one ozone inlet; at least one airflow outlet; and a sterilant delivery device comprising a nebulization element and one or more sterilants, wherein the nebulization element is configured to convert the one or more sterilants into an oxidative aerosol sterilant and deliver the oxidative aerosol sterilant into the instrument receptacle. In an example aspect, the one or more sterilants comprise hydrogen peroxide.

Figure 3:
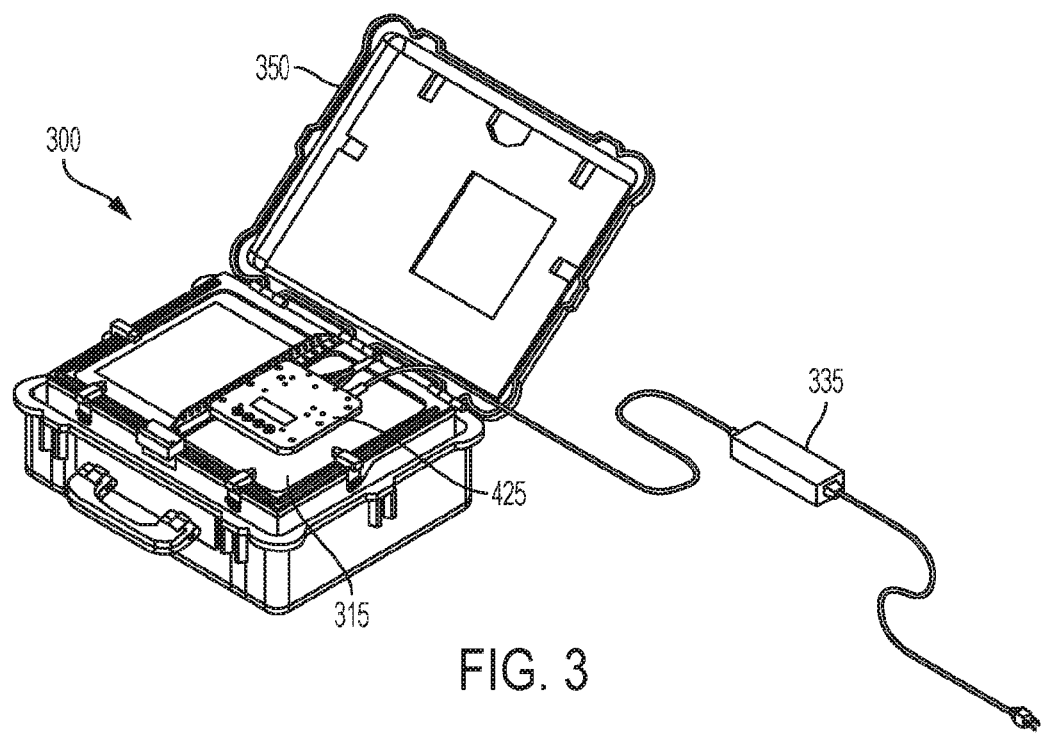
FIG. 3 is a representative illustration of a sterilization top for a sterilization device according to an example aspect.

As illustrated in FIG. 3, sterilization device 300 according to an example aspect includes sterilization top 315. In an example aspect, sterilization top 315 includes output 425 for process feedback and control, error reporting, or other operational messages. Output 425 is also referred to interchangeably herein as control panel or feedback display 425. In an example aspect, the sterilization device further comprises one or more sensors operatively associated with the control panel and configured to monitor one or more operational parameters of the device. In an example aspect, the one or more operational parameters comprise one or more of closure integrity, sterilant levels, ozone levels, airflow velocity, air pressure, valve operation, temperature, humidity, power levels, electrical current, device operation, sterilization cycle lengths, and sterilization cycle number.

In an example aspect, output 425 is an OLED screen, where OLED stands for organic light-emitting diode. Sterilization device 300 may also include inputs such as a keyboard, momentary switches, or a microphone to receive inputs, commands, parameters, etc. and provide operation controls based on such inputs. In an example aspect, sterilization device 300 is configured to request and process inputs and outputs using a software control package. In an example aspect, the software control package is configured to communicate with sensors and use sensor inputs to facilitate a desired operation of the device. In another example aspect, sterilization device 300 is configured to request and process inputs and outputs using an application for a device such as a smart phone or tablet, for example. In an example aspect, an input may include activation of the sterilant breakdown routine entered by a user. In an example aspect, sterilization device 300 includes a software control package configured to automatically trigger the sterilant breakdown routine during the process of operation and in response to any device failures, for example, to abort. The software package optionally includes parameter monitoring and process data storage and record retention and output. It will be appreciated by those of skill in the art that the automation, operation, and/or control of the device may be accomplished by software, hardware, firmware, or a combination thereof. For purposes of the description, the term "software" is interchangeable with hardware, firmware or combinations of software, hardware or firmware.

In an example aspect, the sterilization device or the sterilization chamber or both are optionally configured with controls such as locking mechanisms to prevent opening the device while operating, thereby breaking the seal and causing failure of the sterilization process. In an example aspect, locking controls are configured to require a full sterilant breakdown routine prior to allowing the opening of the case or allowing the release of a vacuum which may be built up within the case. In one embodiment, an operational vacuum acts as a method of leak detection and as a safety provision. In an example aspect, device 300 includes a leak detector to detect leaking from outside the device to inside or vice versa.

Figure 4:
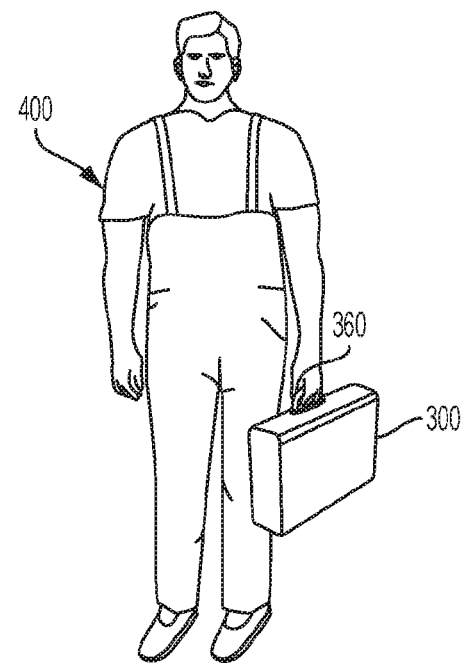
FIG. 4 is a representative illustration of a person carrying a portable sterilization device according to an example aspect.

As illustrated in FIG. 4, sterilization device 300 is configured to be carried by a person, represented by figure 400. Figure 400 can transport the sterilization device easily using handle 360 to wherever the contents, once sterilized, are needed and used. In an example aspect, sterilization device 300 is light weight. In an example aspect, sterilization device 300 is at most 70 pounds. In another example aspect, sterilization device 300 is between about 20 pounds and about 55 pounds. In yet another example aspect, sterilization device 300 is about 38 pounds. As one skilled in the art would appreciate, alternative lighter weight materials or components may be used to make the sterilization device lighter. In an example aspect, the sterilization device is at most 40 pounds. In another example aspect, the sterilization device is at most 30 pounds. In yet another example aspect, the sterilization device is at most 20 pounds.

Figure 5A:
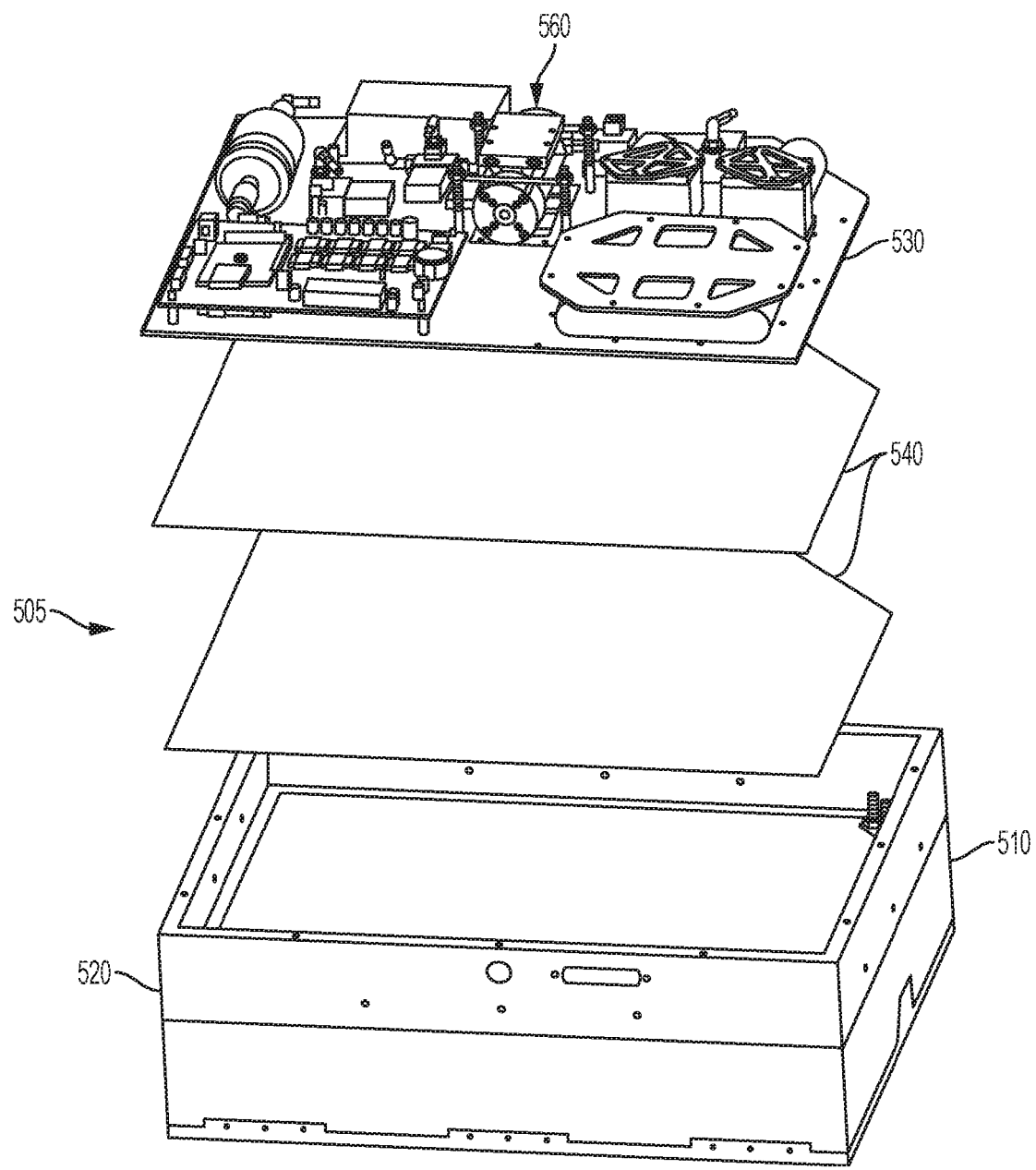
FIG. 5A is a representative illustration exploded view of a components chamber assembly for a sterilization device according to an example aspect.
Figure 5B:
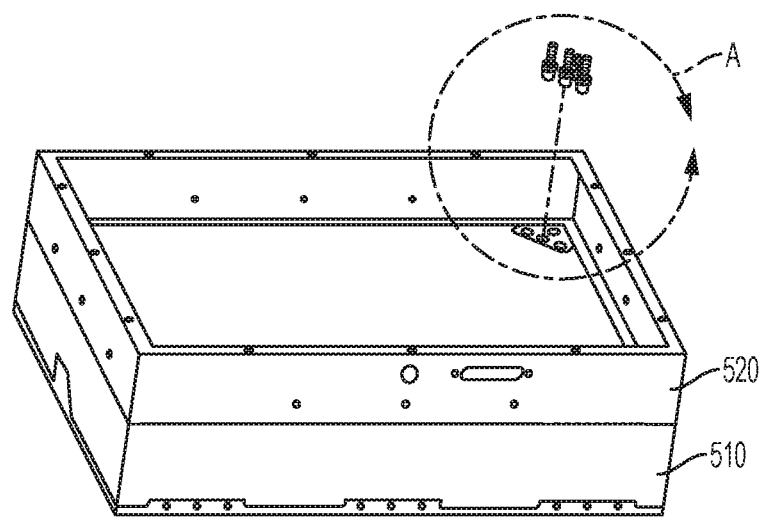
FIG. 5B is a representative illustration of a components chamber assembly having area A for a sterilization device according to an example aspect.
Figure 5C:
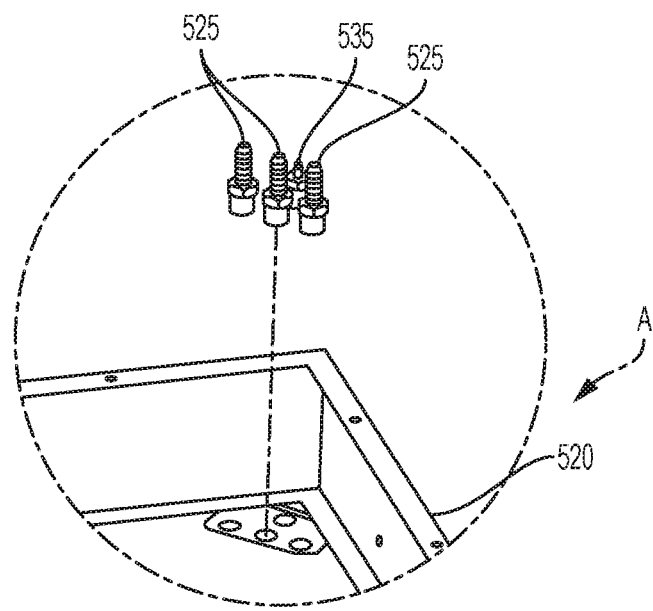
FIG. 5C is a representative illustration of area A as shown in FIG. 5B according to an example aspect.

FIG. 5A is an exploded view of components chamber assembly 520 of assembly of chambers 505. Assembly of chambers 505 includes sterilization chamber 510 and components chamber assembly 520. Components chamber assembly 520 includes mounting sheet assembly 530 and electrical insulating sheets 540. In an example aspect, components chamber assembly 520 serves as a base for sterilization chamber 510. Typically components chamber assembly 520 sits in the bottom of device housing (the housing, for example, case 350 as shown in FIG. 2A). FIG. 5A, in other words, shows the assembly of chambers from the perspective of the bottom of the device. FIG. 5A includes a perspective view of mounting sheet assembly 530 including ozone generator 560. FIG. 5B illustrates area A of components chamber assembly 520 including hose barbs for communication with sterilization chamber 510. FIG. 5C illustrates area A of FIG. 5B in greater detail. Sterilization chamber hose barbs 525 and sterilization chamber vacuum hose barb 535 connect and allow for passage of gases between components chamber assembly 520 and sterilization chamber 510.

Figure 6:
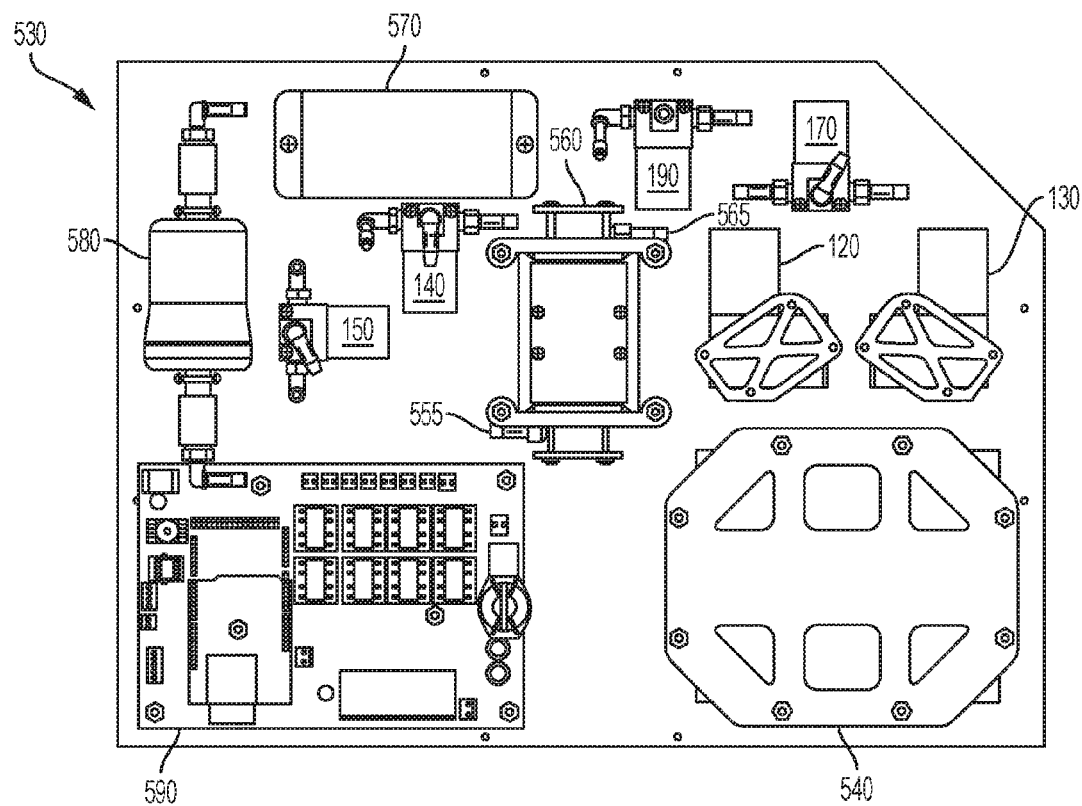
FIG. 6 is a representative illustration of a mounting sheet assembly for a sterilization device according to an example aspect.

Mounting sheet assembly 530, shown as illustrated in top view in FIG. 6, includes ozone generator 560, ozone generator transformer 570, and ozone scrubber 580. Mounting sheet assembly 530 further includes printed circuit board (PCB) 590 and battery 540. Mounting sheet assembly 530 also includes pump assemblies 120 and 130 as well as valves 140, 150, 190, and 170, shown also in FIGS. 1A and 1B.

The sterilization device does not require an external power source. In one embodiment the device includes a battery. As illustrated in FIG. 6, a sterilization device according to an example aspect is operated using battery power. In an example aspect, battery 540 is fixed to mounting sheet assembly 530. In an example aspect, the sterilization device includes an onboard secondary battery that may contain lithium iron phosphate and have a nominal voltage of about 12.8 VDC and about 9.9 AHr of charge capacity. In an example aspect, the battery is rechargeable with the capability to removably connect to an external power source. The battery may have a voltage of less than 18 volts. In one embodiment, the voltage is between about 10 and 15 volts. In one embodiment, the device of the present invention uses a Lithium iron phosphate secondary battery with a nominal voltage of 12.8V and 9.9 A-Hr capacity. The device may include a regulator to regulate the voltage to 12 VDC with a maximum current load of 5 A (60 W). The external power adaptor is configured for domestic and international use and accepts 85-264 VAC, 47-63 Hz providing 14.5 VDC at a max current of 10 A. The device can be charged while in operation at a maximum current of 4 A (58 W). At this rate the battery can be fully recharged in less than 2.5 hours even while running. In one embodiment, the maximum power consumption for running the device while charging is about 118 W.

In an example aspect, the sterilization device also includes adaptors to interface with the battery or power source. In an example aspect, the power source has a VDC (volts of direct current) of between about 9 and about 36 and may have at least about a 6 A discharge current capacity. In an example aspect, the sterilization device is configured with an AC wall adaptor. The wall adaptor is configurable to work with international power sources. Accordingly, the sterilization device is configured to receive power inputs of between about 85 to about 264 VAC, and between about 47 and about 63 Hz.

Figure 7:
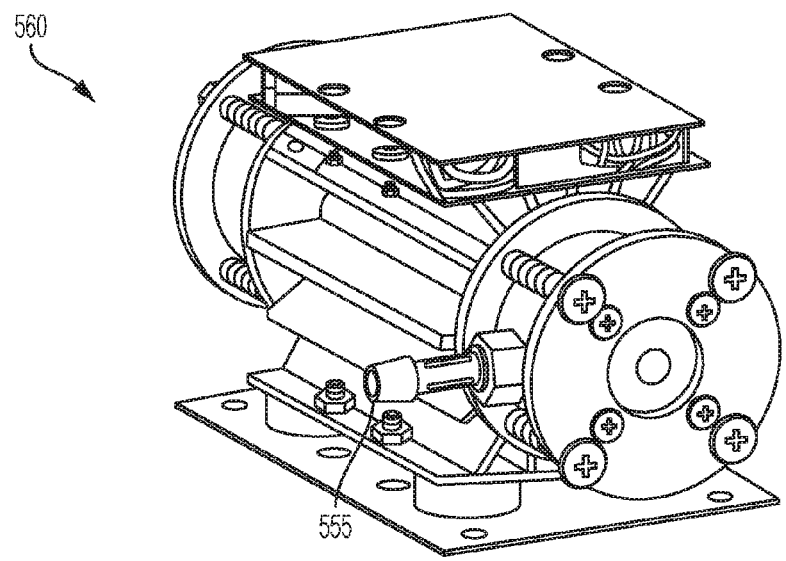
FIG. 7 is a representative illustration of an ozone generator for a sterilization device according to an example aspect.

The sterilization device does not require an oxygen or air source. In an example aspect, the portable sterilization device includes an ozone delivery device, wherein the ozone delivery device comprises a corona discharge ozone generator. Ozone delivery device is referred to as corona discharge ozone generator or ozone generator interchangeably herein. Ozone generator 560, as shown also in FIGS. 5 and 6, is illustrated in FIG. 7. In an example aspect, the sterilization device uses utilizes a synergistic combination of ozone and hydrogen peroxide to produce a potent sterilant that is catalytically decomposed into to oxygen and water vapor at the end of the process. In an example aspect, ozone comes from a corona discharge. The ozone may be generated from ambient air and fed through inlet 555 to ozone generator 560 and out through outlet 565 to inject via tubing to valve 170. Valve 170 also includes an outlet for direct communication with a feed line to the sterilant delivery device or nebulizer, the nebulizer containing an aqueous hydrogen peroxide solution. In an example aspect, valve 170 includes an outlet for injecting air containing ozone to sterilization chamber 110 (or 210, 510). Air containing ozone is fed through valve 170 for simultaneous nebulization with the hydrogen peroxide solution into a vapor. Ozone and hydrogen peroxide vapors are generated and mixed (peroxone) within the sterilization device. The resulting gas plasma contains highly oxidative chemical species. In an example aspect, the reactants used to produce the sterilant include ozone, ambient air, hydrogen peroxide, and water. The reaction produces numerous oxidizing species, transition species, and free radicals as products. The reaction may not be complete however and thus ozone, hydrogen peroxide, air, and water are all also potential products. The concentration of molecular ozone in the sterilization chamber during the sterilization cycle is in the range of 200 to 1500 ppmv based on conditions (relative humidity, pressure, temperature). This is the excess ozone as a product. In an example aspect, between about 200 and about 1500 ppmv of ozone is present. In an example aspect, the portable sterilization device includes an airflow circulation assembly comprising one or more pumps configured to circulate air through the sterilization device. Airflow circulation assembly is referred to as circulation element or circulator interchangeably herein. In an example aspect, the sterilization device includes a circulation element or circulator configured to continuously or intermittently circulate air through the device. The circulation element or circulator includes, for example, pumps, valves, and tubing to circulate the flow of air, ozone, or both through the sterilization device.

In an example aspect, the sterilization chamber for sterilizing a plurality of medical instruments further comprises an ozone delivery device operatively associated with the nebulization element, wherein the ozone delivery device and the nebulization element are configured to deliver the oxidative aerosol sterilant and ozone simultaneously into the instrument receptacle. In an example aspect, the sterilization chamber for sterilizing a plurality of medical instruments further comprises an airflow circulation assembly comprising one or more pumps configured to circulate air through the sterilization chamber.

In an example aspect, the portable sterilization device includes a sealable sterilization chamber located within the external housing unit. As illustrated in FIG. 8, assembly of chambers 505 includes sterilization chamber 510 and components chamber assembly 520 for a sterilization device according to an example aspect. In an example aspect, the sterilization chamber is sealable. Sterilization chamber 510 includes a seal or an o-ring 515 for sealing the sterilization chamber base to a sterilization chamber top (top 315 shown in FIGS. 2B and 2C). In an example aspect, at least a portion of the sterilant delivery device comprises a nebulization element that is contained within the sterilization chamber. Sterilization chamber 510 includes nebulization element 580. The nebulization element is also referred to as a nebulizer, mixer, or mixing element interchangeably herein. In an example aspect, the one or more sterilants comprise hydrogen peroxide contained within the nebulization element. In an example aspect, sterilant delivery device 580 is a nebulizer. In an example aspect, sterilant delivery device 580 is a compressive nebulizer. Sterilant delivery device 580 is associated with base or manifold 575 having ports. In an example aspect, manifold 575 has four ports: two straight and two right angle (90 degree ports). All four ports enter the manifold from the components chamber below via barbed fittings. One straight port enters the nebulizer from valve 170 when it is active. One straight port is open to the chamber and is connected to an air duct within tubing that is in communication with a pressure sensor (chamber pressure). One 90 degree port is open to the chamber providing a path for circulated air that bypasses the nebulizer; this is connected to valve 170 and is open when the valve is not active. One 90 degree port is open to the chamber providing a return path for circulated air. This port is connected to the air pumps which pull air from the chamber to circulate through the system. The air containing ozone, exiting the ozone generator via valve 170, enters nebulizer 580 through manifold 575. The plasma gas sterilant (i.e. ozone) and liquid sterilant (i.e. hydrogen peroxide) are mixed within the nebulizer reservoir, and then further throughout sterilization chamber 510. Reactions are occurring throughout the sterilization chamber.

A sterilant delivery device is shown in detail as illustrated in FIG. 9A. In an example aspect, the sterilant delivery device is nebulizer 580 for a sterilization device. Nebulizer 580 includes body 582 and o-ring 584 for sealing engagement of body 582 with manifold or base 575. Body 582 is also referred to interchangeably herein as a reservoir 582 for holding a liquid sterilant, such as $H_2O_2$. In an example aspect, body 582 is cylindrical. Reservoir 582 is configured for receiving $H_2O_2$ or other liquid sterilant. In an example aspect, the hydrogen peroxide is pre-loaded and contained within the mixing element, or nebulizer 580. Sterilant delivery device 580 further includes removable top 586 having fill port or opening 588 for receiving liquid sterilant. Air containing ozone is received by nebulizer 580 through a feed line through the manifold (not shown). The feed line connects, for example through valves (i.e. 170) and tubing, the components chamber to the sterilization chamber. Air containing ozone exits the ozone generator in the components chamber assembly 520 via valve (valve 170 of FIG. 1B) and then enters the nebulizer through manifold 575. In an example aspect, valve 170 is a solenoid that takes air from the ozone generator and directs it to either the nebulizer through a top port on manifold 575, or bypassing the nebulizer to one of the front ports indicated on manifold 575. Valve 170 is active during the sterilant injection and exposure phases with air directed through the nebulizer. During sterilant breakdown, valve 170 is off, and air is directed to an open port on the front of manifold 575 so that it does not go through the nebulizer. The second open port on the front of manifold 575 is the air return from the chamber which is attached directly to airflow circulation assembly (i.e. pumps 120, 130), which pulls air from sterilization chamber 510 and circulates it through the system. The airflow circulation assembly provides air flow paths through components that are in communication with the sterilization chamber. Barbed fittings, as shown in FIGS. 5B and 5C, are threaded into the underside of manifold 575. Manifold 575 provides channels for the air flow paths into the and out of sterilization chamber 510. Also provided in manifold 575 is a point where the chamber pressure is measured by a first pressure sensor.

Valves, hosing, and fittings as known in the art are useful in transporting the gas plasma sterilant (i.e. air containing ozone) to the nebulizer containing liquid sterilant (i.e. hydrogen peroxide). The plasma gas sterilant is circulated into the nebulizer and in combination with the liquid sterilant is compressively passed through the nebulizer, thus aerosolizing the mixture, for simultaneous delivery into the sterilization chamber. In an example aspect, the compressive means of the nebulizer includes that air containing ozone, leaving valve 170, is forced through a very narrow orifice thereby increasing pressure. The pressure oscillates a collar around the small orifice, which is in communication with the hydrogen peroxide solution. Connected to the air flow path between valve 170 and the narrow constriction within the nebulizer is a second pressure sensor that measures the backpressure produced by the compressive nebulizer. This measurement is useful for process control. As shown also in FIG. 9A, sterilant delivery device 580 includes baffles 592 around nebulizer body 582 to provide additional turbulence to the air flow leaving the nebulizer. This provides better distribution and mixing of the sterilant compounds.

FIG. 9B illustrates a side view of sterilant delivery device 580. In an example aspect, sterilant delivery device 580 is a compressive nebulizer and includes nebulizer fill port 588, top 586, outlet 602, body or reservoir 582, and manifold attachment 604. Nebulizer 580 is filled with a pre-measured volume of dilute hydrogen peroxide.

In an example aspect, hydrogen peroxide is not present in excess once reacted with the gas plasma sterilant (ozone) and thus is optionally left over as a product of the reaction. In an example aspect, the device uses a pre-loaded measure of 4 mL of 7% aqueous hydrogen peroxide (93% water). In an example aspect, the liquid sterilant solution is completely consumed during the mixing process. All of the products are involved in the sterilization mechanism of action to varying degrees. It will be appreciated by those of skill in the art that ozone and peroxide are also extremely potent for pollution abatement and will decompose any organic compounds in the ambient air.

In some embodiments, hydrogen peroxide constitutes all or part of a liquid sterilant useful in the sterilization device. Hydrogen peroxide, in the form of hydrogen peroxide dose packets, is pre-loaded in the sterilization device. In an example aspect, the hydrogen peroxide dose may be 4 mL of 7% aqueous hydrogen peroxide sealed in a packet or container. In an example aspect, the packet of hydrogen peroxide contains aqueous hydrogen peroxide ($H_2O_2$ and deionized water), including hydrogen peroxide ranging between 3% and 30% aqueous hydrogen peroxide. In another example aspect, the hydrogen peroxide is at most 8% aqueous hydrogen peroxide. In yet another example aspect, the hydrogen peroxide is about 7% aqueous hydrogen peroxide. The packets of hydrogen peroxide are filled and heat sealed. In an example aspect, the packet is configured such that the user can tear the packet open and add it to a nebulizer reservoir in the sterilization chamber prior to operation. For example, one entire packet is conveniently used for each sterilization cycle.

Generally, the sterilants of the present disclosure generate reactive oxygen species (ROS) which can be used to kill various microbes, microorganisms, and pathogens. The phrase "reactive oxygen species" is used to describe a number of reactive molecules and free radicals derived from molecular oxygen. Their reactivity is generally due to their presence of an unpaired electron, which has potent degradation effects on a wide variety of substances. This degradation effect can often be measured in terms of a chemical's oxidation potential (e.g., the oxidative capacity of a given oxidizing agent). Molecular oxygen can be used to generate a number of ROS, including but not limited to, peroxide, hydrogen peroxide, nitric oxide, an oxygen ion, a hydroxyl ion, a hydroxyl radical, and superoxide, as shown below.

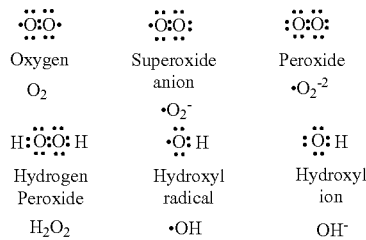

In some embodiments, the presence of a catalyst can augment the production of various ROS by shifting the dynamic equilibrium of a ROS reaction to the production of free radicals that can degrade various biomass materials. For example, in one embodiment of the present disclosure, hydrogen peroxide can be used to generate hydroxyl radicals in the presence of a transition metal catalyst. Without being limited to a particular catalyst, embodiments of the present disclosure can include catalysts that are comprised of one or more transition metals, such as but not limited to, Scandium, Titanium, Vanadium, Chromium, Manganese, Iron, Cobalt, Nickel, Copper, Zinc, Yttrium, Zirconium, Niobium, Molybdenum, Technetium, Ruthenium, Rhodium, Palladium, Silver, Cadmium, Hafnium, Tantalum, Tungsten, Rhenium, Osmium, Iridium, Platinum, Gold, Mercury, Rutherfordium, Dubnium, Seaborgium, Bohrium, Hassium, Meitnerium, Ununnilium, Unununium, and Ununbium. Additionally, as would be readily recognized by one of ordinary skill in the art based on the present disclosure, catalysts of the present disclosure can be any heterogeneous mixture and/or combination of the above transitional metals, and may include other components that augment the catalytic process and the production of ROS. In some embodiments of the present disclosure, the catalyst is an iron-based catalyst and the iron-based catalyst interacts chemically with hydrogen peroxide in an aqueous solution to produce hydroxyl radicals that reduce the number of colony forming units (CFUs) for a given microbe or pathogen.

In some embodiments, the nebulization element is configured to be operatively associated with an ozone generator to produce ROS and to deliver ROS into the sterilization chamber simultaneously and continuously. In some embodiments, ozone generated from the ozone generator can directly enter the nebulization element such that the ozone and the hydrogen peroxide present in the nebulization element are aerosolized and react chemically to form ROS. For example, in one embodiment, ozone and water can react within the nebulization element and throughout the sterilization chamber to kill various microbes, microorganisms, and pathogens. The chemical reaction of ozone and water can form various oxidizing products, including $HO_3^+$, hydroxide, and hydroperoxyl, as shown below.

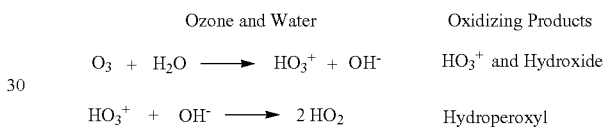

In another embodiment, ozone and hydrogen peroxide (e.g., peroxone) can react within the nebulization element and throughout the sterilization chamber to kill various microbes, microorganisms, and pathogens. The chemical reaction of ozone and hydrogen peroxide can form various oxidizing products, including various hydroxyl radicals, as shown below.

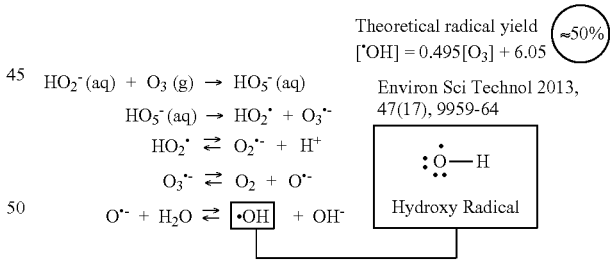

The continuous production of the various oxidizing products from ozone and hydrogen peroxide by the devices and methods of the present disclosure can result in the synergistic elimination of pathogenic microorganisms. For example, the continuous production of oxidizing products from ozone and hydrogen peroxide by the devices and methods of the present disclosure can reduce both the overall quantities of pathogenic microorganisms and can reduce a greater variety of pathogenic microorganisms than exposure to either ozone or aerosolized hydrogen peroxide alone. In some cases, the continuous production of ROS from ozone and hydrogen peroxide by the devices and methods of the present disclosure can reduce the amount and varieties of pathogenic microorganisms in less time than exposure to either ozone or aerosolized hydrogen peroxide alone. In an example aspect, the number of survivors is negatively correlated with increased hydrogen peroxide concentrations. In an example aspect in the range of 0 to 35% $H_2O_2$ by volume, the greater the concentration the more effective the sterilant.

In one embodiment, the sterilization devices and methods of the present disclosure can inactivate a 6 log population of microorganisms determined to be most resistant organisms (MRO) to sterilization. For example, the sterilization devices and methods of the present disclosure can inactivate a 6 log population of (*Geobacillus Stearothermophilus*), identified as most resistant to the process, in 7.5 minutes of sterilant exposure time. In another example, stainless steel (316L) material coupons processed in the sterilization device of the present disclosure for 5 consecutive cycles received the best possible score of 0 when tested for cytotoxicity using the standard MEM elution protocol, wherein MEM stands for minimum essential medium. In yet another example, the simultaneous and continuous delivery of the oxidative aerosol sterilant and the ozone into the sterilization chamber containing a plurality of medical instruments at a pre-determined ozone concentration for a pre-determined time period is sufficient to obtain a sterility assurance level (SAL) of $10^{-6}$ for inactivation of a 6 log population of organisms determined to be most resistant organisms (MRO) to sterilization. In an example aspect, the sterilization device meets or exceeds criteria for passing of systemic toxicity: systemic injection, systemic toxicity: material mediated pyrogen, irritation: intracutaneous toxicity, cytotoxicity, and sensitization.

In an example aspect, the sterilization device includes a chemical indicator or other measurement element to determine or provide a measure of sterilant efficacy or other parameter. The chemical indicator or measurement element provides a parameter indicator of one or more separate elements of the sterilant. In an example aspect, a chemical indicator changes color under oxidation signifying a certain level of sterilant or sterilant component efficacy. Other indicators useful in the sterilization device include organic dyes that turn a lighter color, for example, when oxidized and/or in the presence of humidity. The user, or the device through a sensor, compares the color to a reference ring surrounding the indicator to determine if the process was effective. In an example aspect, chemical indicators are useful as a method or process validation and record retention (routine process monitoring) to demonstrate specified process conditions were met.

In an example aspect, the portable sterilization device further comprises a sterilant remediation element, wherein the sterilant remediation element and the airflow circulation assembly are operatively associated with the sealable sterilization chamber; and wherein the airflow circulation assembly is configured to cause air to flow from the sterilization chamber through the sterilant remediation element such that the air comprising the combination of the one or more sterilants and the ozone passes through the sterilant remediation element to facilitate breakdown of the one or more sterilants and the ozone into oxygen and water. In an example aspect, sterilant remediation element is referred to as breakdown catalyst interchangeably herein. In an example aspect, the sterilization device is configured to allow for an active breakdown of sterilant with catalyst after sterilization has taken place. This ensures minimizing the concentration of potentially harmful ozone vapors in the sterilization chamber and provides for safely opening the device for the removal of sterilized surgical instruments. In an example aspect, the sterilant remediation element comprises a metal-based catalyst that facilitates breakdown of the one or more sterilants and the ozone into oxygen and water. In an example aspect, the catalysts include one or more of manganese dioxide and copper oxide. In an example aspect, the sterilant is ozone. In another example aspect, the sterilant is a mixture of ozone and filtered local air circulating through the device.

In an example aspect, air is circulated through the sterilization device. In one embodiment, the sterilization device is configured to pull air from the sterilization chamber and direct it through tubing to components. This may be accomplished in a variety of ways, including using air pumps. Valves determine the flow path as controlled by a custom circuit board and software. In an example aspect, the valves include 3-way solenoid valves. The activation and inactivation of all components is controlled through a microprocessor that activates solid state relays to provide power to the component. In an example aspect, the power provided to each component is regulated to be consistently 12 VDC to maintain process consistency. During the sterilant generation and exposure phases, air is continuously circuited through a corona discharge ozone generator and then directly to the compressive nebulizer containing hydrogen peroxide within the sterilization chamber. The mixed sterilant is produced with the nebulizer as ozone reacts with hydrogen peroxide and water vapor but continues to be formed in cascading reactions within the sterilization chamber and on the surfaces of instruments. During the sterilant breakdown phase, air is diverted through the breakdown catalyst and continuously circulated until the ozone and peroxide concentrations are reduced to safe levels decomposing into oxygen and water vapor. In an example aspect, air leaving the catalyst is returned to the sterilization chamber though a separate port to circumvent the nebulizer. Multiple pumps can be used during the breakdown phase to increase the decomposition rate as the air is circulated faster through the device. In an example aspect, entries (intake, nebulizer, exhaust, pressure duct) to the hermetically welded sterilization chamber are though an aluminum manifold.

In an example aspect, there is a continuous mixing of hydrogen peroxide and ozone throughout the sterilization process. In an example aspect, dilute aqueous hydrogen peroxide is used; for example, the hydrogen peroxide may be less than 8% by volume. In other example aspects, hydrogen peroxide, ozone, and water are used to react together to form the sterilant. In an example aspect, the sterilant comprises a highly oxidative species. In an example aspect, the sterilant mixture is dispersed with a compressive nebulizer.

Figure 1B:
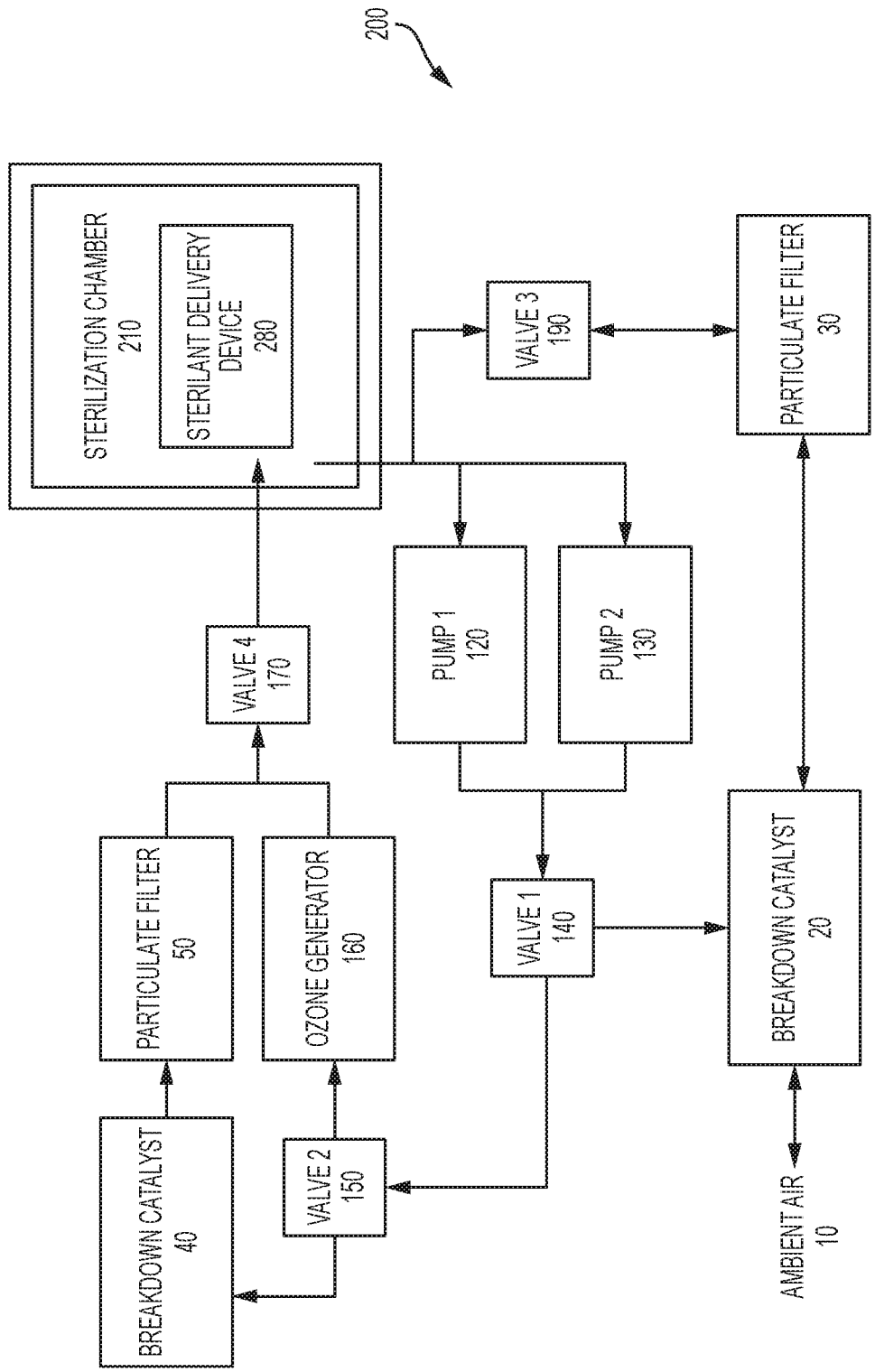
FIG. 1B is a representative illustration of a block flow diagram according to another aspect of the invention.

The sterilization process is performed using ambient air. In an example aspect, the air being used is the air residing inside the housing or case of the device. Thus, the sterilization device does not require supplemental air. In an example aspect, the device uses air with less than about 30% oxygen content. In an example aspect, the air is filtered inside the device as it circulates using an air filter or a particulate filter (30, 50 as shown in FIGS. 1A and 1B). The device of the present invention is configured such that no external oxygen source is required, no external water source is required, and no potable water is required. Accordingly, the case or housing of the device can be manufactured without inputs or connection fittings for these sources making manufacture easier and cheaper and facilitating the portability of the device and superior ingress protection.

In an example aspect, the device is configured to actively decompose the sterilant after use into oxygen and water vapor using a true catalyst, or in other words, a catalyst that is not consumed by the reaction. Accordingly, the catalyst need not be replaced or regenerated. In an example aspect, air is retained in the device as it is circulated through the catalyst until the amount of sterilant in the device reaches OSHA acceptable concentrations. This is an advantage over other devices that vent the ozone through a catalyst to the external environment because, for example, in prior art devices, air only passes once through a catalyst, which may be inefficient and insufficient to completely decompose the sterilant. The present sterilization device renders an ozone concentration that is harmless before opening of the sterilization device and releasing into the environment.

In an example aspect, the catalyst used to decompose the sterilant includes one or more of manganese dioxide and copper oxide. In embodiment that catalyst may be sold under the trademark HOPCALITE® owned by Mine Safety Appliance Company Corporation. In other example aspects, the catalyst is sold under the trademark CARULITE® owned by Carus Corporation.

The device hardware and software is designed to meet FDA requirements for sterilization of medical devices. Primarily that it consistently achieves lethality conditions for inactivation of organisms determined to be most resistant (MRO) to the process. The process is specified to achieve a sterility assurance level (SAL) of 10-6 for inactivation of a 6 log population of the MRO, or the probability of 1 survivor out of every 1,000,000 sterilization cycles. The most resistant organism to chemical and thermal sterilization processes is identified by the CDC and FDA as *Geobacillus stearothermophilus*. Biological indicators containing greater than a 6 log population of the MRO have been tested to determine the time required for inactivation under the device process conditions. Samples were exposed to the process for specified durations then transferred to growth media to determine whether any viable organisms remain. The samples are then incubated at optimal conditions for 7 days. If there are any viable organisms the solution will become turbid. If after 7 days the solution remains clear it is determined that all of the colony forming units (CFU) were inactivated. This Boolean (Pass or Fail) result indicates that the process was sufficient to inactivate a 6 log population. Sterilant exposure durations of 7.5 minutes have resulted in no growth of the indicator organism after 7 days of incubation. For FDA compliance the exposure time if then at minimum doubled to attain <overkill>, resulting in a SAL of 10-6.

Process conditions are controlled and monitored by the device during operation. Current sensors are used to measure the ozone generator load. The device is continuously monitoring feedback from these sensors to determine whether the generator output is within specified bounds. The applied potential of all active electrical components (solenoid valves, pumps, and ozone generator) is controlled at a constant 12 VDC via an onboard voltage regulator. The device will take a wide input range as low as 9 VDC and up to 250 VAC with the external power adaptor. An internal secondary battery can be used to power the device without an external power source. The battery state of charge is calculated with a fuel gauge integrated circuit (IC). The state of charge calculation is recorded in the data file and used for operational feedback. The device will prevent operation if the battery level is insufficient for an entire cycle when the external adaptor is not connected. When the power adaptor is connected a charge controller IC will limit the charging current to 4 A and indicate to the user that the battery is charging. With the power adaptor the device will charge the internal battery and can be operated simultaneously. A pressure transducer is connected to the sterilization chamber to measure vacuum level of the sterilization chamber relative to ambient. This sensor is used for leak detection. During operation the software continuously checks the relative vacuum, if the value is outside of the predetermined thresholds the device automatically initiates the sterilant breakdown routine and indicating to the user that the sterilization chamber pressure went out of range. Any sensor feedback indicating that the process conditions are out of a predetermined range will initiate the sterilant breakdown routine to permit safe opening. There is a different pressure transducer connected to the air flow path between the ozone generator and the nebulizer within the sterilization chamber. Feedback from this transducer serves two purposes. During ozone generation phases (injection and exposure) a backpressure develops in the space where the sensor is attached due to the nebulizer constriction. If the nebulizer is malfunctioning or not properly attached the backpressure in this branch will be minimal or non-existent. If the backpressure value is outside of predetermined bounds during ozone generation phases the device will initiate the breakdown routine and indicate to the user that the nebulizer is not attached correctly. The backpressure reading will also confirm that the valve upstream of the ozone generator is functioning properly and that the air flow within the device is compliant with the design parameters. If the valve is malfunctioning such that the air flow path is incorrect or partially obstructed the backpressure value will be out of range. Similar control and feedback systems are in place for sterilization chamber relative humidity, and temperature.

The device is intended for use in a wide range of environments. The device has been tested under numerous environmental conditions and is believed to be validated as safe and effective (as a sterilizer) over a specified range of ambient temperature, ambient humidity, and barometric pressure. The device utilizes onboard sensors to measure all of these values in real time. This feedback is incorporated into the device operation and recorded in the header of data files for subsequent sterilization cycles. If any of the ambient temperature, ambient humidity, or barometric pressure readings are outside of the predetermined bounds the device will prevent initiation of a sterilization cycle and notify the user which of the condition are out of range.

Once the sterilant exposure and breakdown phases are complete the device will stop and indicate to the user that the load is sterile and ready for use. The device will maintain the relative vacuum within the sterilization chamber for a predetermined period or until the user acknowledges the feedback and presses a button to permit opening of the sterilization chamber and use of the sterilized instruments. This feature allows for the sterilization chamber to act as one large sterile barrier for a predetermined duration following sterilization in the event that the user is not ready to use the instruments that were sterilized. The sterile barrier will be tested using an aerosolized spore suspension with a method known as the package integrity test standard for sterile barriers and packaging.

Figure 10:
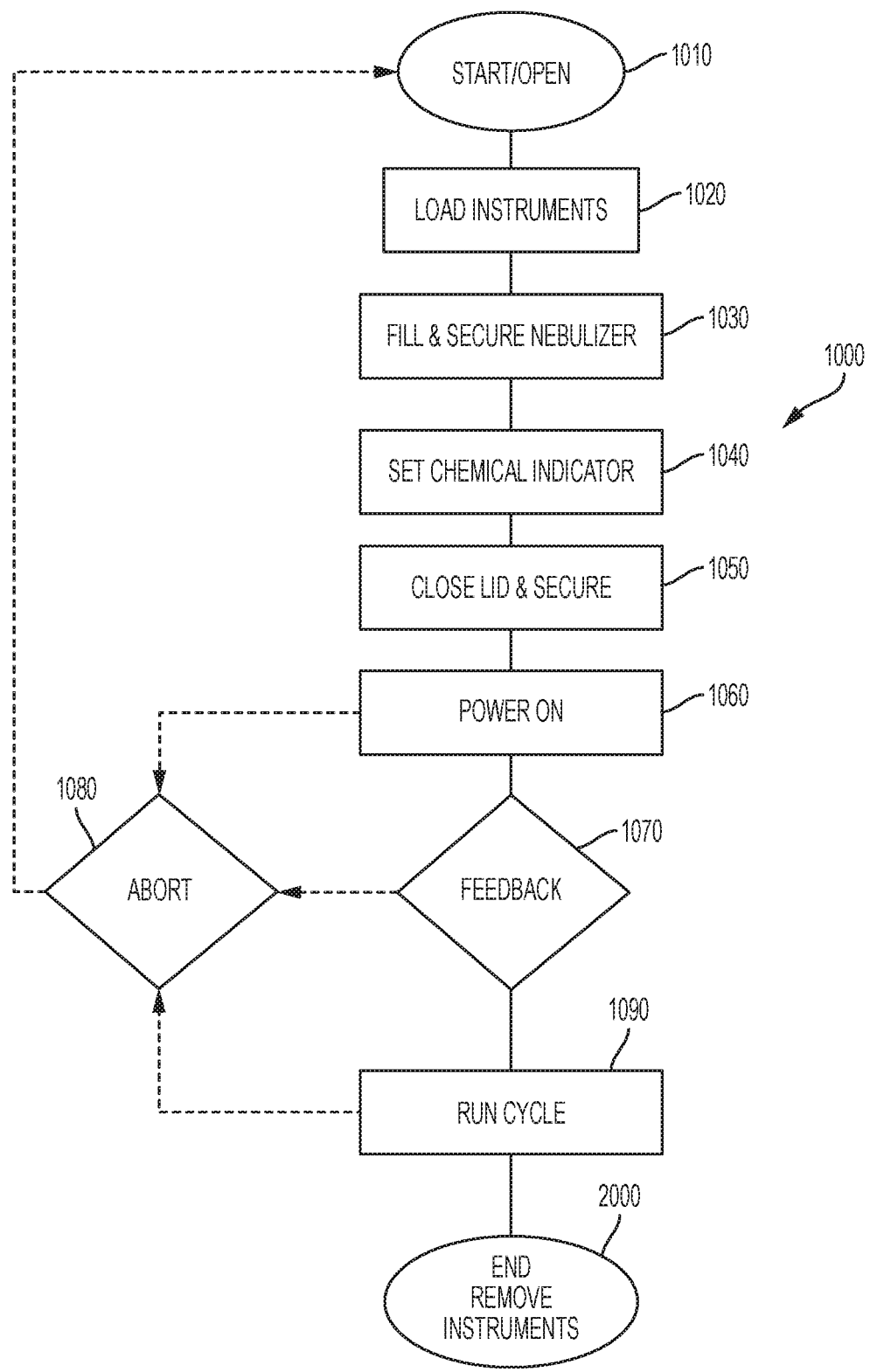
FIG. 10 is a flow chart illustrating use of the sterilization device according to an example aspect.

FIG. 10 is a flow chart illustrating use and operation of the sterilization device according to an example aspect. At any time, if needed, a user can abort a cycle at step 1080 and run the breakdown phase. Safety features prevent the system from opening until breakdown phase is finished. A user prepares the sterilizer for use by setting the case on a level or substantially level surface, opening external latches on housing or case, and lifting the lid to expose the sterilization top. Then the user opens the four internal latches and lifts the sterilization chamber lid to inspect the chamber, which should be clean and dry, as in step 1010. The user then loads the sterilization chamber with cleaned and dry stainless steel and/or tungsten carbide surgical instruments, for example, as in step 1020. Instruments should be spaced so that the instruments are not touching and all jaws and clamps are open and not engaged. In step 1030, user checks that the sterilant delivery device or nebulizer is completely empty and dry. If needed, sterile dressing is used to dry the reservoir. The user then adds the entire contents of one ROSS M1 solution sachet (7% hydrogen peroxide) into the nebulizer reservoir. The user then ensures nebulizer top is placed securely on base and secured firmly to manifold. In step 1040, the user optionally places a chemical indicator face up in front left corner of chamber. The user then closes the sterilization chamber lid and secures all four latches as in step 1050. The user then presses the power switch on the control panel to power the device ON in step 1060. To initialize the sterilization device, the user presses and holds the 'Wake' button for 3 seconds. To start a cycle, from the main menu, the user presses and holds the 'Start' button for 3 seconds. As in step 1070, the feedback display then prompts the user to press 'Yes' to confirm ROSS M1 solution was added. Feedback display also prompts the user to press 'Yes' to start cycle 'Automated Operation', as in step 1090. Step 1090 includes the breakdown cycle to return the sterilization chamber to a safe level of ozone. When complete, two tones sound and the feedback display reads 'Sterilization Complete', at which time the user presses 'Yes' to Open, and then instruments may be removed in step 2000, with the instruments available at that time for immediate use. As mentioned, sterilization process may be aborted if needed as in step 1080. To initiate the sterilant breakdown phase at any time, the user presses and holds the red 'Abort' button for 3 seconds, at which time the system will display: 'ERROR: Aborted, Ozone Above PEL, Do Not Open'. In an example aspect, the system will prevent normal operation if there is an initial vacuum within the chamber. The system will display: ERROR: Chamber Pressurized, at which time the user runs the breakdown phase to return sterilant concentrations to a safe level and equilibrate the chamber pressure. In the event of power failure, the user holds the 'Abort' button for 3 seconds to initiate the sterilant breakdown phase from the main menu. The load is not ready for use and must be reprocessed. In the event the battery dies during operation, the user switches OFF the power, attaches the power adaptor, plugs in the power supply, switches ON the power, wakes the device (hold wake for 3 seconds), and initiates the breakdown phase (hold Abort for 3 seconds). In the event power is not available, the user leaves the system closed and inactive until the device can be connected to power.

In an example aspect a method comprising manufacturing a portable sterilization device comprising is provided. In an example aspect, the method includes manufacturing a portable sterilization device comprising an external housing unit; a sealable sterilization chamber located within the external housing unit; a sterilant delivery device operatively associated with the sterilization chamber, the sterilant delivery device comprising a nebulization element and one or more sterilants, wherein the nebulization element is configured to convert the one or more sterilants into an oxidative aerosol sterilant and deliver the oxidative aerosol sterilant into the sterilization chamber; an ozone delivery device operatively associated with the sterilization chamber and the sterilant delivery device, the ozone delivery device configured to deliver ozone into the sterilization chamber; an airflow circulation assembly; a control panel configured to operate the sterilization chamber, the sterilant delivery device, the ozone delivery device, and the airflow circulation assembly, wherein the control panel is further configured to execute an operation to deliver the oxidative aerosol sterilant and the ozone simultaneously into the sterilization chamber; and a power source operatively associated with the control panel and configured to supply power to the sterilization chamber, the sterilant delivery device, the ozone delivery device, and the airflow circulation assembly.

In an example aspect, the method includes wherein at least a portion of the one or more sterilants comprise hydrogen peroxide. In an example aspect, the method includes wherein the sterilant delivery device comprising the nebulization element is contained within the sterilization chamber. In another example aspect, the method includes wherein the sterilant delivery device comprising the nebulization element is at least partially contained within the sterilization chamber. In yet another example aspect, the method includes wherein at least a portion of the sterilant delivery device (such as at least a portion of the nebulization element, such as outlet 602 or a portion thereof) is contained within the sterilization chamber. In an example aspect, the method includes wherein the one or more sterilants comprise hydrogen peroxide contained within the nebulization element. In an example aspect, the method includes wherein the ozone delivery device comprises a corona discharge ozone generator. In an example aspect, the method includes wherein the airflow circulation assembly comprises one or more pumps configured to circulate air through the sterilization device. In an example aspect, the method includes wherein the portable sterilization device further comprises a sterilant remediation element, wherein the sterilant remediation element and the airflow circulation assembly are operatively associated with the sealable sterilization chamber; and wherein the airflow circulation assembly is configured to cause air to flow from the sterilization chamber through the sterilant remediation element such that the air comprising the combination of the one or more sterilants and the ozone passes through the sterilant remediation element to facilitate breakdown of the one or more sterilants and the ozone into oxygen and water. In an example aspect, the method includes wherein the sterilant remediation element comprises a metal-based catalyst that facilitates breakdown of the one or more sterilants and the ozone into oxygen and water. In an example aspect, the method includes wherein the portable sterilization device further comprises one or more sensors operatively associated with the control panel and configured to monitor one or more operational parameters of the device. In an example aspect, the method includes wherein the one or more operational parameters comprise one or more of closure integrity, sterilant levels, ozone levels, airflow velocity, air pressure, valve operation, temperature, humidity, power levels, electrical current, device operation, sterilization cycle lengths, and sterilization cycle number.

At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting aspects or features of the embodiment(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_l$, and an upper limit, $R_u$, is disclosed, any number falling within the range is specifically disclosed. In particular, the following numbers within the range are specifically disclosed: $R=R_l+k*(R_u-R_l)$, wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent.

Moreover, any numerical range defined by two R numbers as defined in the above is also specifically disclosed. Use of the term "optionally" with respect to any element of a claim means that the element is required, or alternatively, the element is not required, both alternatives being within the scope of the claim. Use of broader terms such as comprises, includes, and having should be understood to provide support for narrower terms such as consisting of, consisting essentially of, and comprised substantially of. Accordingly, the scope of protection is not limited by the description set out above but is defined by the claims that follow, that scope including all equivalents of the subject matter of the claims. Each and every claim is incorporated as further disclosure into the specification and the claims are embodiment(s) of the present disclosure.

The present disclosure, in various aspects, embodiments, and configurations, includes components, methods, processes, systems and/or apparatus substantially as depicted and described herein, including various aspects, embodiments, configurations, sub combinations, and subsets thereof. Those of skill in the art will understand how to make and use the various aspects, aspects, embodiments, and configurations, after understanding the present disclosure. The present disclosure, in various aspects, embodiments, and configurations, includes providing compositions and processes in the absence of items not depicted and/or described herein or in various aspects, embodiments, and configurations hereof, including in the absence of such items as may have been used in previous compositions or processes, e.g., for improving performance, achieving ease and\or reducing cost of implementation.

EXAMPLES

The sterilization device includes a global power switch, which the user presses on a user interface to provide power to a circuit board. The power switch is SPST (single pole, single throw), although a DPST (double pole, single throw) switch is also suitable. The user presses, holds, and releases the wake button (momentary switch, ON) on the user interface. The device becomes active, runs a component bit check routine, and displays a main menu. From the main menu the user can press a process info button to view sensor measurements including ambient temperature, ambient humidity, barometric pressure, battery state of charge (%), device temperature, ozone generator current, total current, and sterilization chamber pressure. The user can also press and hold an 'Abort' button to run the sterilant breakdown routine from the main menu and at any time during operation. When the sterilant breakdown routine is automatically triggered through device error or by pressing the abort button the device will indicate to the user that the load is not sterile and must be reprocessed. To start a sterilization cycle the user can press, hold, and release a 'Start' button. The device will then prompt the user to confirm whether the hydrogen peroxide solution was added. If the user has not added solution the device will return to the main menu. Once added and user confirmed the device will ask to confirm start of the cycle. Once cycle start has been confirmed it will automatically begin the process. During all process phases the device will display the phase number, phase name, phase time remaining, and total time remaining on the user interface. The user can also use a 'Process Info' button to view all of the sensor measurements in real time.

A Phase 0 begins as the device then opens valve 1 and activates pump 1 which pulls air from the sterilization chamber and evacuates it to the external environment through a filter and breakdown catalyst. After a predetermined time the device checks the relative vacuum pressure of the sterilization chamber to confirm sufficient seal, pump, and valve operation. If the vacuum is within the specified bounds the device then continues to a Phase 1.

Phase 1 is sterilant injection. The device turns off valve 1 sealing off the external environment. During this phase all valves are off with pump 1 on. Air is pulled from the sterilization chamber and circulated through the ozone generator and through the compressive nebulizer back into the sterilization chamber. Ozone is continuously generated and injected into an aqueous solution of hydrogen peroxide in the nebulizer which creates an oxidative aerosol. The injection phase is specified to reach a predetermined ozone concentration within the sterilization chamber. After a predetermined time a Phase 2 begins.

Phase 2 is sterilant exposure. The exposure phase time is determined by FDA requirements for <overkill> to reach a SAL of 10−6 otherwise the operation is identical to Phase 1. Once the exposure phase is complete a Phase 3 begins.

Phase 3 is sterilant breakdown. The device activates valve 2 which diverts air from the ozone generation branch to the breakdown catalyst branch. Pump 2 is activated with Pump 1 so that both are running simultaneously to increase the flow rate and increase the rate of sterilant decomposition. Air is continuously pulled from the sterilization chamber, circulated through the breakdown branch, and returned to the sterilization chamber for a predetermined duration to return sterilant concentrations to safe levels for human exposure (OSHA permitted exposure levels). After the predetermined time the device will indicate to the user that the process is complete, the load is sterile and ready for use. A timer will display how long the load can remain in the sterile barrier if needed prior to use. When ready the user can acknowledge the completion prompt and the sterilization chamber will vent back to ambient pressure to permit opening. After the cycle is complete the device closes and saves the data file including a log of the pass/fail determination and sensor readings then returns to standby. In one embodiment, the Device maintains a partial vacuum in the sterilization chamber of between about 1 PSIV and about 2 PSIV. Increasing the vacuum rating of the device provides greater diffusion capabilities and more rapid inactivation of contaminant microorganisms. At greater vacuum levels the device could provide the capability for sterilization of products such as packaged (porous Tyvek) instruments and devices with lumens. The Device may also be configured with a port to utilize supplemental oxygen or greater power for ozone production. In these cases process times could be reduced and throughput increased. The higher the oxygen concentration the higher the ozone concentration as the ozone is generated from oxygen molecules. The sterilant efficacy is improved with increased ozone concentration. Greater sterilant efficacy allows for more rapid inactivation of biological species permitting a shorter cycle time. Each component of the device that is in contact with the sterilant is configured to be non-reactive with the type of sterilant being used. In one embodiment, where the sterilant is a mixture of Ozone and hydrogen peroxide, the oxidizing nature of the sterilant however dictates that components that come in contact with the ozone be of a material that is compatible with this gas. In one embodiment, the components may comprise one or more of stainless steel (316L), anodized aluminum, Teflon, Kynar, PEEK, EPDM, Norprene, medical grade silicone, fluorosilicone, HDPE, UHMWPE, glasses and ceramics, titanium. The Device eliminates many risks associated with current chemical sterilization methods, reduces the overall logistics of chemical and thermal sterilization, and reduces the overall time needed to sterilize surgical instruments.

Figure 11:
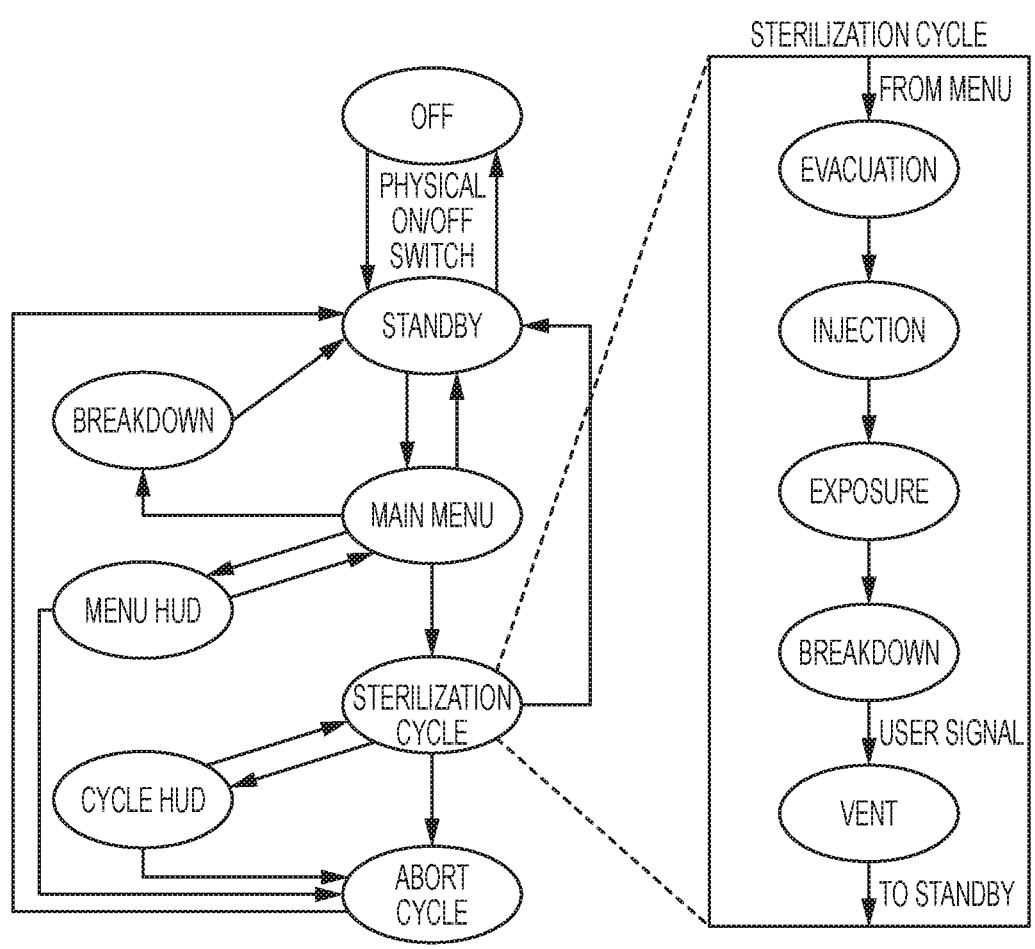
FIG. 11 is a flow chart illustrating the Rugged Ozone Sterilization System (ROSS) software state diagram according to an example aspect; and, FIG. 12 is a schematic illustrating the sterilization device component interface connections according to an example aspect.

A Rugged Ozone Sterilization System (ROSS) software state diagram is provided in FIG. 11. Directionality of arrow indicates a one directional state transition. Various states of the sterilization cycle are shown at right. The transition between the Off and Standby states is mediated by a physical switch as opposed to a change in software state. While most of the transitions between subsequent stages in the Sterilization Cycle state are timed, the final transition is initiated by user input. Most other transitions among states in the diagram result from stimuli provided by the user.

Figure 12:
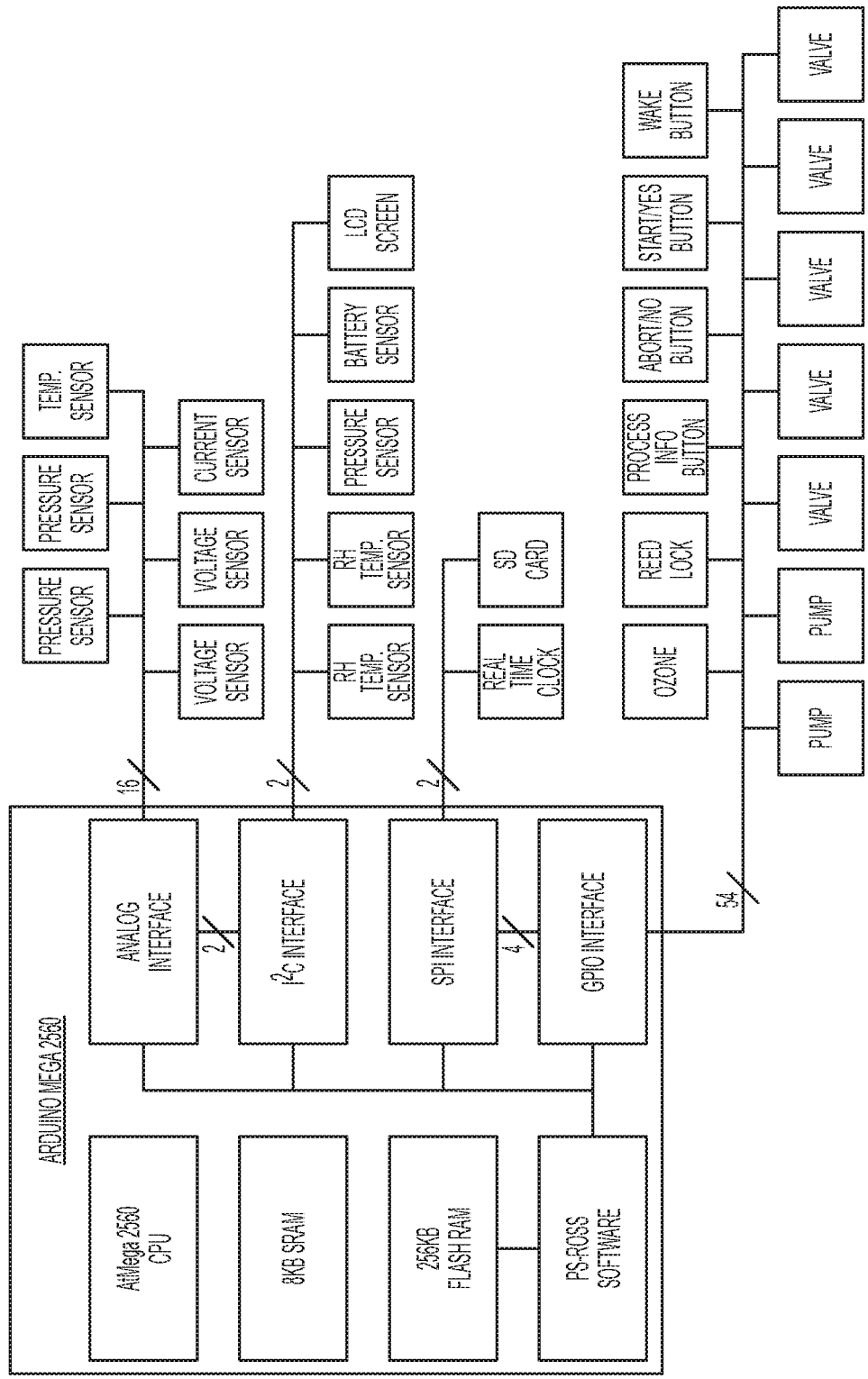

A schematic of sterilization device component interface connections is provided in FIG. 12.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more, aspects, embodiments, and configurations for the purpose of streamlining the disclosure. The features of the aspects, embodiments, and configurations of the disclosure may be combined in alternate aspects, embodiments, and configurations other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed aspects, embodiments, and configurations. Thus, the following claims are hereby incorporated into this Detailed Description, with each claim standing on its own as a separate preferred embodiment of the disclosure.

Moreover, though the description of the disclosure has included description of one or more aspects, embodiments, or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A portable sterilization device for use with one or more sterilants, the portable sterilization device comprising:
an external housing unit including disposed within the external housing unit:
a sealable sterilization chamber, the sealable sterilization chamber configured to have an atmosphere contained therein;
an ozone delivery device operatively associated with the sealable sterilization chamber, the ozone delivery device configured to generate a plasma gas sterilant;
a sterilant delivery device operatively associated with the sealable sterilization chamber and the ozone delivery device, the sterilant delivery device comprising a nebulization element, wherein the nebulization element is configured to receive the plasma gas sterilant and convert by nebulization the one or more sterilants with the plasma gas sterilant into an oxidative aerosol sterilant and is further configured to deliver the oxidative aerosol sterilant into the sealable sterilization chamber;
a circulator including a pathway from the ozone delivery device in direct communication with the nebulizer and configured to direct portions of the atmosphere from the sealable sterilization chamber to the ozone delivery device and back to the sealable sterilization chamber;
a control panel configured to operate the sealable sterilization chamber, the sterilant delivery device, the ozone delivery device, and the circulator; and
a power source operatively associated with the control panel and configured to supply power to at least the sterilant delivery device, the ozone delivery device, and the circulator;
whereupon activation, the control panel is configured to execute an operation to provide delivery of the oxidative aerosol sterilant into the sealable sterilization chamber.

2. The portable sterilization device of claim 1, wherein the sealable sterilization chamber is configured to accept a plurality of medical instruments, and wherein the delivery of the oxidative aerosol sterilant into the sealable sterilization chamber containing the plurality of medical instruments at a pre-determined ozone concentration for a pre-determined time period is sufficient to obtain a sterility assurance level (SAL) of $10^{-6}$ for inactivation of a 6 log population of organisms determined to be most resistant organisms (MRO) to sterilization.

3. The portable sterilization device of claim 1, wherein at least a portion of the sterilant delivery device comprising the nebulization element is contained within the sealable sterilization chamber.

4. The portable sterilization device of claim 1, wherein the nebulization element is configured to receive hydrogen peroxide.

5. The portable sterilization device of claim 1, wherein the ozone delivery device comprises a corona discharge ozone generator.

6. The portable sterilization device of claim 1, wherein the circulator comprises one or more pumps configured to circulate the atmosphere through the sealable sterilization chamber.

7. The portable sterilization device of claim 1, further comprising a sterilant remediation element, wherein the sterilant remediation element and the circulator are operatively associated with the sealable sterilization chamber; and wherein the circulator is configured to cause the atmosphere to flow from the sealable sterilization chamber through the sterilant remediation element such that the atmosphere comprising the oxidative aerosol sterilant passes through the sterilant remediation element which is configured to facilitate a breakdown of the oxidative aerosol sterilant into oxygen and water.

8. The portable sterilization device of claim 7, wherein the sterilant remediation element comprises a metal-based catalyst that is configured to facilitate the breakdown of the oxidative aerosol sterilant into oxygen and water.

9. The portable sterilization device of claim 1, further comprising one or more sensors operatively associated with the control panel and configured to monitor one or more operational parameters.

10. The portable sterilization device of claim 9, wherein the one or more operational parameters comprise one or more of closure integrity, sterilant levels, ozone levels, airflow velocity, air pressure, valve operation, temperature, humidity, power levels, electrical current, device operation, sterilization cycle lengths, and sterilization cycle number.

11. An article for sterilizing a plurality of medical instruments comprising:
a sterilization chamber including a sterilization chamber base, a sterilization chamber top, and a seal located between the sterilization chamber base and the sterilization chamber top, wherein the sterilization chamber top is moveable relative to the sterilization chamber base;
a sterilant delivery device comprising a nebulization element contained within the sterilization chamber;
wherein the sterilant delivery device further comprises a manifold associated with the nebulization element, the manifold including at least one ozone inlet and at least one airflow outlet, the nebulization element configured to receive a plasma gas sterilant via the at least one ozone inlet and at least one liquid sterilant, wherein the nebulization element is further configured to convert the plasma gas sterilant and the at least one liquid sterilant into an oxidative aerosol sterilant and release the oxidative aerosol sterilant within the sterilization chamber.

12. The article of claim 11, wherein the at least one liquid sterilant is hydrogen peroxide.

13. A method comprising:
manufacturing a portable sterilization device comprising:
an external housing unit including disposed within the external housing unit:
a sealable sterilization chamber, the sealable sterilization chamber configured to have an atmosphere contained therein;
an ozone delivery device operatively associated with the sealable sterilization chamber, the ozone delivery device configured to generate a plasma gas sterilant;
a sterilant delivery device operatively associated with the sealable sterilization chamber and the ozone delivery device, the sterilant delivery device comprising a nebulization element and configured to receive one or more sterilants, wherein the nebulization element is further configured to receive the plasma gas sterilant and convert by nebulization the one or more sterilants with the plasma gas sterilant into an oxidative aerosol sterilant and is further configured to deliver the oxidative aerosol sterilant into the sealable sterilization chamber;
a circulator including a pathway from the ozone delivery device in direct communication with the nebulizer and configured to direct portions of the atmosphere from the sealable sterilization chamber to the ozone delivery device and back to the sealable sterilization chamber;
a control panel configured to operate the sealable sterilization chamber, the sterilant delivery device, the ozone delivery device, and the circulator; and
a power source operatively associated with the control panel and configured to supply power to at least the sterilant delivery device, the ozone delivery device, and the circulator.

14. The method of claim 13, wherein the sterilant delivery device is configured to receive hydrogen peroxide.

15. The method of claim 14, wherein the sterilant delivery device comprising the nebulization element is configured to receive hydrogen peroxide contained within the nebulization element.

16. The method of claim 13, wherein the sterilant delivery device comprising the nebulization element is at least partially contained within the sealable sterilization chamber.

17. The method of claim 13, wherein the ozone delivery device comprises a corona discharge ozone generator.

18. The method of claim 13, wherein the circulator comprises one or more pumps configured to circulate the atmosphere through the sealable sterilization chamber.

19. The method of claim 13, wherein the portable sterilization device further comprises a sterilant remediation element, wherein the sterilant remediation element and the circulator are operatively associated with the sealable sterilization chamber; and
wherein the circulator is configured to cause the atmosphere to flow from the sterilization chamber through the sterilant remediation element such that the atmosphere comprising the oxidative aerosol sterilant passes through the sterilant remediation element which is configured to facilitate a breakdown of the oxidative aerosol sterilant into oxygen and water.

20. The method of claim 19, wherein the sterilant remediation element comprises a metal-based catalyst that is configured to facilitate the breakdown of the oxidative aerosol sterilant into oxygen and water.

21. The method of claim 20, wherein the portable sterilization device further comprises one or more sensors operatively associated with the control panel and configured to monitor one or more operational parameters.

22. The method of claim 21, wherein the one or more operational parameters comprise one or more of closure integrity, sterilant levels, ozone levels, airflow velocity, air pressure, valve operation, temperature, humidity, power levels, electrical current, device operation, sterilization cycle lengths, and sterilization cycle number.

23. A portable sterilization device comprising:
an external housing unit including disposed within the external housing unit:
a sealable sterilization chamber, the sealable sterilization chamber configured to have an atmosphere contained therein;
an ozone delivery device operatively associated with the sealable sterilization chamber, the ozone delivery device configured to generate a plasma gas sterilant;
a sterilant delivery device operatively associated with the sealable sterilization chamber and the ozone delivery device, the sterilant delivery device comprising a nebulization element and one or more sterilants, wherein the nebulization element is configured to receive the plasma gas sterilant and convert by nebulization the one or more sterilants with the plasma gas sterilant into an oxidative aerosol sterilant and deliver the oxidative aerosol sterilant into the sealable sterilization chamber;
a circulator including a pathway from the ozone delivery device in direct communication with the nebulizer and configured to direct portions of the atmosphere from the sealable sterilization chamber to the ozone delivery device and back to the sealable sterilization chamber;
a control panel configured to operate the sealable sterilization chamber, the sterilant delivery device, the ozone delivery device, and the circulator; and
a power source operatively associated with the control panel and configured to supply power to at least the sterilant delivery device, the ozone delivery device, and the circulator;
whereupon activation, the control panel is configured to execute an operation to provide delivery of the oxidative aerosol sterilant into the sealable sterilization chamber; and,
wherein the portable sterilization device is self-contained within the external housing unit and does not include an external water source and an external oxygen source.

24. The portable sterilization device of claim 23, wherein the sealable sterilization chamber is configured to accept a plurality of medical instruments, and wherein the delivery of the oxidative aerosol sterilant into the sterilization chamber containing the plurality of medical instruments at a pre-determined ozone concentration for a pre-determined time period is sufficient to obtain a sterility assurance level (SAL) of $10^{-6}$ for inactivation of a 6 log population of organisms determined to be most resistant organisms (MRO) to sterilization.

25. The portable sterilization device of claim 23, wherein the one or more sterilants comprise hydrogen peroxide, and wherein at least a portion of the sterilant delivery device comprising the nebulization element is contained within the sealable sterilization chamber.

26. The portable sterilization device of claim 23, wherein the one or more sterilants comprise hydrogen peroxide contained within the nebulization element.

27. The portable sterilization device of claim 23, further comprising a sterilant remediation element, wherein the sterilant remediation element and the circulator are operatively associated with the sealable sterilization chamber; and wherein the circulator is configured to cause the atmosphere to flow from the sealable sterilization chamber through the sterilant remediation element such that the atmosphere comprising the oxidative aerosol sterilant passes through the sterilant remediation element to facilitate a breakdown of the oxidative aerosol sterilant into oxygen and water.

28. The portable sterilization device of claim 27, wherein the sterilant remediation element comprises a metal-based catalyst that facilitates the breakdown of the oxidative aerosol sterilant into oxygen and water.

* * * * *